United States Patent
Humes et al.

(10) Patent No.: US 7,332,330 B2
(45) Date of Patent: Feb. 19, 2008

(54) DEVICE FOR MAINTAINING VASCULARIZATION NEAR AN IMPLANT

(75) Inventors: H. David Humes, Ann Arbor, MI (US); William H. Fissell, Whitmore Lake, MI (US); Deborah A. Buffington, Ann Arbor, MI (US); Evangelos Tziampazis, Plymouth, MI (US)

(73) Assignee: RenaMed Biologics, Inc., Lincoln, RI (US)

( * ) Notice: Subject to any disclaimer, the term of this patent is extended or adjusted under 35 U.S.C. 154(b) by 253 days.

(21) Appl. No.: 09/949,575

(22) Filed: Sep. 11, 2001

(65) Prior Publication Data

US 2003/0050622 A1    Mar. 13, 2003

(51) Int. Cl.
*C12M 3/06* (2006.01)
*A61F 2/00* (2006.01)
*C12N 5/02* (2006.01)
*C12N 11/04* (2006.01)

(52) U.S. Cl. .................. 435/297.1; 424/423; 435/182; 435/283.1

(58) Field of Classification Search ................ 424/423; 435/177, 180, 395
See application file for complete search history.

(56) References Cited

U.S. PATENT DOCUMENTS

| | | | |
|---|---|---|---|
| 3,734,851 A | | 5/1973 | Matsumura |
| 4,242,460 A | | 12/1980 | Chick et al. |
| 4,354,933 A | | 10/1982 | Lester |
| 4,973,493 A | | 11/1990 | Guire |
| 5,002,582 A | | 3/1991 | Guire et al. |
| 5,360,790 A | | 11/1994 | Humes |
| 5,414,075 A | | 5/1995 | Swan et al. |
| 5,429,938 A | | 7/1995 | Humes |
| 5,437,994 A | | 8/1995 | Emerson et al. |
| 5,459,069 A | | 10/1995 | Palsson et al. |
| 5,499,976 A | * | 3/1996 | Dalton ........................ 604/180 |
| 5,516,680 A | | 5/1996 | Naughton et al. |
| 5,549,674 A | | 8/1996 | Humes et al. |
| 5,550,050 A | | 8/1996 | Holland et al. |
| 5,580,697 A | | 12/1996 | Keana et al. |
| 5,605,822 A | | 2/1997 | Emerson et al. |
| 5,639,275 A | | 6/1997 | Baetge et al. |
| 5,653,975 A | | 8/1997 | Baetge et al. |
| 5,656,481 A | | 8/1997 | Baetge et al. |
| 5,661,133 A | * | 8/1997 | Leiden et al. .................. 514/44 |
| 5,676,943 A | | 10/1997 | Baetge et al. |
| 5,686,289 A | | 11/1997 | Humes et al. |
| 5,733,727 A | | 3/1998 | Field |
| 5,763,266 A | | 6/1998 | Palsson et al. |
| 5,773,286 A | | 6/1998 | Dionne et al. |
| 5,795,790 A | | 8/1998 | Schinstine et al. |
| 5,833,978 A | | 11/1998 | Tremblay |
| 5,843,781 A | | 12/1998 | Ballermann et al. ........ 435/400 |
| 5,858,653 A | | 1/1999 | Duran et al. |
| 5,906,817 A | | 5/1999 | Moullier et al. |
| 5,919,449 A | | 7/1999 | Dinsmore |
| 5,965,125 A | * | 10/1999 | Mineau-Hanschke .... 424/93.21 |
| 6,060,270 A | | 5/2000 | Humes |
| 6,110,209 A | * | 8/2000 | Stone ........................ 623/16.11 |
| 6,150,164 A | | 11/2000 | Humes |
| 6,156,304 A | * | 12/2000 | Glorioso et al. ............ 424/93.2 |

FOREIGN PATENT DOCUMENTS

| | | |
|---|---|---|
| GB | 1 479 002 | 6/1974 |
| WO | WO 89/01967 | 3/1989 |
| WO | WO 91/00119 | 1/1991 |
| WO | WO 92/07615 | 5/1992 |
| WO | WO 93/17696 | 9/1993 |

OTHER PUBLICATIONS

H. David Humes et al., *Replacement of Renal Function in Uremic Animals with a Tissue-Engineered Kidney*, Nature Biotechnology. vol. 17, pp. 451-455, May 1999.

Roger C. Bone, *Systemic Inflammatory Response Syndrome: A Unifying Concept of Systemic Inflammation. Sepsis and Multiorgan Failure*, 1997. pp. 3-10.

H. David Humes et al., *Tissue Engineering of a Bioartificial Renal Tubule Assist Device: In Vitro Transport and Metabolic Characteristics*, Kidney International, vol. 55 (1999), pp. 2502-2514.

H. David Humes, *Bioartificial Kidney for Full Renal Replacement Therapy*, Seminars in Nephrology. vol. 20, No. 1, Jan. 2000, pp. 71-82.

John M. Walker et al. *The Language of Biotechnology*. 1988. p. 126.
R. Ian Freshney. *Culture of Animal Cells, A Manual of Basic Technique*. Second Edition. 1987. pp. 1-13. and pp. 197-206.
Sherrill M. MacKay et al., *Tissue Engineering of a Bioartificial Renal Tubule*. ASAIO Journal. vol. 44. No. 3. May-Jun. 1998. pp. 179-183.
Sally Pobojewski, *U Researchers Unveil Component of Bio-Artificial Kidney*, The University Record May 24, 1999.
Charles Natansonet et al., *Role of Endotoxemia in Cardiovascular Dysfunction and Mortality*, The Journal of Clinical Investigation, Inc., vol. 83, Jan. 1989, pp. 243-251.
Bradley D. Freeman et al., *Continuous Arteriovenous Hemofiltration Does Not Improve Survival in a Canine Model of Septic Shock*, Journal of the American College of Surgeons, Mar. 1995, vol. 180, pp. 286-291.
J. A. Kellum, *Immunomodulation in Sepsis: The Role of Hemofiltration*, Minerva Anestesiologica. vol. 65, No. 6, pp. 410-418.

(Continued)

Primary Examiner—David M. Naff
(74) Attorney, Agent, or Firm—Hamilton, Brook, Smith & Reynolds, P.C.

(57) ABSTRACT

A device and a method of maintaining vascularization near an implant, especially a bioartificial hemofilter. By associating cells that excrete angiogenic factors with such an implant, vascularization to the tissue surrounding the implant can be maintained. In a bioartificial hemofilter, this facilitates filtrate transport to a collection fiber for drainage from the body. The cells can be genetically engineered, for example using an adenovirus vector encoding for vascular endothelial growth factor. Myoblasts and myotubes may be used in one embodiment of the present invention.

35 Claims, 15 Drawing Sheets

OTHER PUBLICATIONS

Gordon R. Bernard, M.D. et al., *Efficacy and Safety of Recombinant Human Activated Protein C for Severe Sepsis*, The New England Journal of Medicine, vol. 344, No. 10, Mar. 8, 2001, pp. 699-709.

Diep D. Tranet et al., *Age, Chronic Disease, Sepsis, Organ System Failure, and Mortality in a Medical Intensive Care Unit*. Critical Care Medicine, vol. 18, No. 5, pp. 474-479, May 1990.

S. C. Donnellyet et al., *Mediators, Mechanisms and Mortality in Major Trauma*, Resuscitation, vol. 28, pp. 87-92, 1994.

Roger C. Bone, M.D. et al., *A Controlled Clinical Trial of High-Dose Methylprednisolone in the Treatment of Severe Sepsis and Septic Shock*, The New England Journal of Medicine, vol. 317, No. 11, pp. 653-658.

K. D. Horn, *Evolving Strategies in the Treatment of Sepsis and Systemic Inflammatory Response Syndrome (SIRS)*, Q. J. Med, 1998, vol. 91, pp. 265-277.

Michael R. Pinsky, *Serum Cytokine Levels in Human Septic Shock*, Chest, vol. 103, No. 2, Feb. 1993, pp. 565-575.

Claire Marty et al., *Circulating Interleukin-8 Concentrations in Patients with Multiple Organ Failure of Septic and Nonseptic Origin*, Critical Care Medicine, vol. 22, No. 4, pp. 673-679, Apr. 1994.

Pierre Damas, M.D, Ph.D. et al., *Tumor Necrosis Factor and Interleukin-1 Serum Levels During Severe Sepsis in Humans*, Critical Care Medicine, vol. 17, No. 10, pp. 975-978, Oct. 1989.

Charles A. Dinarello, *The Proinflammatory Cytokines Interleukin-1 and Tumor Necrosis Factor and Treatment of the Septic Shock Syndrome*, The Journal of Infectious Diseases, 1991: 163, pp. 1177-1184.

Thierry Calandra et al., *Prognostic Values of Tumor Necrosis Factor/Cachectin, Interleukin-1, Interferon-α, and Interferon-γ in the Serum of Patients with Septic Shock*, The Journal of Infectious Diseases, 1990: 161, pp. 982-987.

J. X. Jiang et al., *Plasma Cytokines and Endotoxin Levels in Patients with Severe Injury and Their Relationship With Organ Damage*, Injury, vol. 28, No. 8, pp. 509-513, 1997.

Dorothy Breen et al., *Acute Renal Failure as a Part of Multiple Organ Failure: The Slippery Slope of Critical Illness*, Kidney International. vol. 53, Suppl. 66 (1998), pp. S-25-S33.

Mark J. Sarnak et al , *Mortality Caused by Sepsis in Patients with End-Stage Renal Disease Compared with the General Population*, Kidney International, vol. 58 (2000), pp. 1758-1764.

Matthias Girndt et al., *Production in Interleukin-6, Tumor Necrosis Factor α and Interleukin-10 in vitro Correlates with the Clinical Immune Defect in Chronic Hemodialysis Patients*, Kidney International, vol. 47 (1995), pp. 559-565.

Matthias Girndt et al., *Impaired Cellular Immune Function in Patients with End-Stage Renal Failure*, Nephrol Dial Transplant, (1999) 14: 2807-2810.

Melissa K. Thomas, M.D., Ph.D. et al., *Hyptovitaminosis D in Medical Inpatients*, The New England Journal of Medicine. vol. 338, No. 12, Mar. 19, 1998, pp. 777-783.

H. David Humes et al., *Replacement of Renal Function in Uremic Animals with a Tissue-Engineered Kidney*. Nature Biotechnology, vol. 17, May 1999, pp. 451-455.

Roger C. Bone, M.D., *Why Sepsis Trials Fail*, JAMA, Aug. 21, 1996, vol. 276, No. 7, pp. 565-566.

Roger C. Bone, M.D., *Toward a Theory Regarding the Pathogenesis of the Systemic Inflammatory Response Syndrome: What we Do and Do Not Know about Cytokine Regulation*, Crit Care Med, 1996, vol. 24, No. 1, pp. 163-172.

C. Erik Hack et al., *Interleukin-8 in Sepsis: Relation to Shock and Inflammatory Mediators*, Infection and Immunity, Jul. 1992, vol. 60, No. 7, p. 2835-2842.

Roger C. Bone, M.D., *Immunologic Dissonance: A Continuing Evolution in Our Understanding of the Systemic Inflammatory Response Syndrome (SIRS) And the Multiple Organ Dysfunction Syndrome (MODS)*, Ann Intern Med., 1996, vol. 125, p. 680-687.

Roger C. Bone, M.D., *Sepsis: A New Hypothesis for Pathogenesis of the Disease Process*, Chest, vol. 112, No. 1, Jul. 1997, pp. 235-243.

John H. Reeveset et al., *Continuous Plasmafiltration in Sepsis Syndrome*, Crit Care Med, 1999, vol. 27, No. 10, pp. 2096-2104.

An S. De Vriese et al., *Continuous Renal Replacement Therapies in Sepsis: Where are the Data?*, Nephrol Dial Transplant, (1998), vol. 13, pp. 1362-1364.

Jean-Louis Vincent, M.D. et al., *Phase II Multicenter Clinical Study of the Platelet-Activating Factor Receptor Antagonist BB-882 in the Treatment of Sepsis*, Crit Care Med, vol. 28, No. 3, 2000. pp. 638-642.

Zenaide M. N. Quezadoet et al., *New Strategies for Combatting Sepsis: The Magic Bullets Missed the Mark . . . But the Search Continues*, Tibtech, Feb. 1995, vol. 13, pp. 56-63.

John W. Christman, M.D., *Strategies for Blocking the Systemic Effects of Cytokines in the Sepsis Syndrome*, Critical Care Medicine, vol. 23, No. 5, pp. 955-963, 1995.

M. L. Kielaret et al., *The Liver Regulates Renal Ischemic Injury: A Possible Role for Renal IL6 and Hepatic IL10?*, Abstract.

Kevin P. Lailyet et al., *The Role of Anti-Tumor Necrosis Factor-α and Interleukin-10 in Protecting Murine Neonates from Escherichia coli, Sepsis*, Journal of Pediatric Surgery. vol. 35, No. 6, Jun. 2000, pp. 852-855.

Keith R. Walley et al., *Balance of Inflammatory Cytokines Related to Severity and Mortality of Murine Sepsis*, Infection and Immunity, No. 1996, pp. 4733-4738, vol. 64, No. 11.

Tetsuya Matsumoto et al., *Effect of Interleukin-10 on Gut-Derived Sepsis Caused by Pseudomonas Aeruginosa in Mice*, Antimicrobial Agents and Chemotherapy, Nov. 1998, vol. 42, No. 11, p. 2853-2857.

Arnaud Merchant et al., *Interleukin-10 Controsl Interferon-γ and Tumor Necrosis Factor Production During Experimetnal Endotoxemia*, Eur. J. Immunol., 1994, vol. 24, pp. 1167-1171.

Sherril M. MacKay et al., *Tissue Engineering of a Bioartificial Renal Tubule*, ASAIO Journal, 1998, pp. 179-183.

Ziad A. Massy, *Reversal of Hyperhomocyst(e) Inaemia in Chronic Renal Failure—Is Folic or Folinic Acid the Answer?*, Nephrol Dial Transplant, (1999), vol. 14, pp. 2810-2812.

Raymond Vanholder et al., *p-Cresol: A Toxin Revealing Many Neglected But Relevant Aspects of Uraemic Toxicity*, Nephrol Dial Transplant (1999) vol. 14, pp. 2813-2815.

Jürgen Bommer, *Saving Erythropoietin by Administering L-Carnitine?*, Nephrol Dial Transplant, (1999), vol. 14, pp. 2819-2821.

Max Dratwa, *Pre-Emptive (CAPD—What Are the Arguments?*, Nephrol Dial Transplant, (1999), vol. 14, pp. 2822-2823.

Bart D. Maes et al., *Anti-Interleukin-2 Receptor Monoclonal Antibodies in Renal Transplantation*, Nephrol Dial Transplant, (1999) vol. 14, pp. 2824-2826.

Andras Mogyorosi et al., *GLUT1 and TGF-β: The Link Between Hyperglycaemia and Diabetic Nephropathy*, Nephrol Dial Transplant, (1999), vol. 14, pp. 2827-2829.

R. Montesano et al., *Induction of Eipthelial Tubular Morphogenesis in Vitro by Fibroblast-Derived Soluble Factors*, Cell, vol. 66, Aug. 23, 1991, pp. 697-711.

H. David Humes et al., *Effects of Transforming Growth Factor-β, Transforming Growth Factor-α, and Other Growth Factors on Renal Proximal Tubule Cells*, Laboratory Investigation, vol. 64, No. 4, pp. 538-545, 1991.

Fiona M. Wattet et al., *Out of Eden: Stem Cells and Their Niches*, Science, vol. 287, Feb. 25, 2000, pp. 1427-1430.

Qais Al-Awqati, *Cellular and Molecular Mechanism of Renal Development and Tubulogenesis*, Current Science, 1062, 4813, Oct., pp. 53-58.

Stuart H. Orkin, M.D., *Report and Recommendations of the Panel to Assess the NIH Investment in Research on Gene Therapy*.

Tze Kin Ip et al., *Renal Epithelial-Cell-Controlled Solute Transport Across Permeable Membranes as the Foundation for a Bioartificial Kidney*, Artificial Organs. vol. 13, No. 1, pp. 58-65, 1989.

Elliot L. Chaikof, *Engineering and Materil Considerations in Islet Cell Transplantation*, Annu. Rev. Biomed. Eng., 01: 103-127, 1999.

Abbie M. Jensen, et al., *Expression of Sonic hedgehog and Its Putative Role as a Putative Role as a Precursor Cell Mitogen in the Developing Mouse Retina*, Development, 124, 363-371, 1997.

Mark J. Horney et al., *Elevated Glucose Increases Mesangial Cell Sensitivity to Insulin-Like Growth Factor I*. The American Physiological Society, pp. F1045-F1053, 1998.

Barry M Brenner, M.D., et al., *Mechanics of Glomerular Ultrafiltration*, The New England Journal of Medicine, vol. 297, 1977, pp. 148-154.

James A. Swiebel, et al., *High-Level Recombinant Gene Expression in Rabbit Endothelial Cells Transduced by Retroviral Vectors*, Science, vol. 243, pp. 220-222.

David A. Dichek, M.D., et al., *Seeding of Intravascular Stents With Genetically Engineered Endothelial Cells*, Circulation, vol. 80, No. 5, Nov. 1989, pp. 1347-1353.

Barry M. Brenner, M.D., et al., *Molecular Basis of Proteinuria of Glomerular Origin*, The New England Journal of Medicine, Apr. 13, 1978, vol. 298, No. 15, pp. 826-833.

Lonnie D. Shea, et al., *DNA Delivery From Polymer Matrices for Tissue Engineering*, Nature Biotechnology, vol. 17, Jun. 1999, pp. 551-554.

Mickey C.-T. Hu, et al., *FGF-18, a Novel Member of the Fibroblast Growth Factor Family, Stimulates Hepatic and Intestinal Proliferation*, Molecular and Cellular Biology, Oct. 1998, pp. 6063-6074, vol. 18, No. 10.

Judah Folkman, et al., *Angiogenesis*, The Journal of Biological Chemistry, vol. 267, No. 16, Jun. 1992, pp. 10931-10934.

Joseph A. Madri, et al., *Phenotypic Modulation of Endothelial Cells by Transforming Growth Factor-β Depends Upon the Composition and Organization of the Extracellular Matrix*, The Journal of Cell Biology, vol. 106, Apr. 1988, pp. 1375-1384.

Yukio Tsurumi, M.D., et al., *Direct Intramuscular Gene Transfer of Naked DNA Encoding Vascular Endothelial Growth Factor Augments Collateral Development and Tissue Perfusion*, Circulation, vol. 94, No. 12, Dec. 15, 1996, pp. 3281-3290.

Shailen R. Patel, et al., *Safety of Direct Myocardial Administration of an Adenovirus Vector Encoding Vascular Endothelial Growth Factor 121*, Human Gene Therapy. vol. 10, 1331-1348, May 20, 1999.

John A. Thompson, et al., *Site-Directed Neovessel Formation in Vivo*, Reports, vol. 241, Sep. 9, 1988, pp. 1349-1352.

James M. Wilson, et al., *Implantation of Vascular Grafts Lines with Genetically Modified Endothelial Cells*. Science, vol. 244, pp. 1344-1346, Jun. 16, 1989.

G. Allen Brady et al., *Solid Freeform Fabrication of Ceramics via Stereolithography*, Department of Materials Science, University of Michigan, 1998, pp. 39-43.

Benedikt Busse et al., *Bioreactors for Hybrid Liver Support: Historical Aspects and Novel Designs, Busse & Gerlach: Bioreactors for Hybrid Liver Support*, Annals New York Academy of Sciences, pp. 326-339.

N. Trivedi, et al., *Improved Vascularization of Planar Membrane Diffusion Devices Following Continuous Infusion of Vascular Endothelial Growth Factor*, Cell Transplantation, vol. 9, pp. 115-124, 2000.

David L. Bourell, et al., *Solid Freeform Fabrication Symposium*, Aug. 12-14, 1996, The University of Texas at Austin.

Duane Dimos et al., *Solid Freeform and Additive Fabrication*, Materials Research Society Symposium Proceedings, vol. 542, Nov. 30-Dec. 1, 1998.

Yuko Tsurumi, M.D., et al., *Direct Intramuscular Gene Transfer of Naked DNA Encoding Vascular Endothelial Growth Factor Augments Collateral Development and Tissue Perfusion*, Circulation, vol. 94, No. 12, Dec. 15, 1996, pp. 3281-3290.

Paul F. Jacobs, Ph.D., *Stereolithography and Other RP&M Technologies for Rapid Prototyping to Rapid Tooling*. Society of Manufacturing Engineers. ASME Press, New York, NY, 1996, pp. 1-392.

Voldman, et al., "Microfabrication in Biology and Medicine", Annu. Rev. Biomed. Eng.:1(1), pp. 401-425, 1999.

B.R. Olsen, "Matrix Molecules and Their Ligands", Principles of Tissue Engineering, pp. 48-65, 1997.

R. Calaflore, et al., "Coherent Microcapsules for Pancreatic Islet Transplantation: A New Approach for Bioartificial Pancreas", Transplantation Proceedings, vol. 28, No. 2, (Apr.), 1996: pp. 812-813.

H. Hayashi, et al., "Long Survival of Xenografted Bioartificial Pancrease with a Mesh-Reinforced Polyvinyl Alcohol Hydrogel Bag Employing a B-Cell Line (MIN6)", Transplantation Proceedings, vol. 28, No. 3 (Jun.), 1996: pp. 1428-1429.

K. Naruse, et al., "Efficacy of a Bioreactor Filled with Porcine Hepatocytes Immobilized on Nonwoven Fabric for Ex Vivo Direct Hemoperfusion Treatment of Liver Failure in Pigs", International Society for Artificial Organs, 22(12): pp. 1031-1037, Blackwell Science, Inc., 1998.

C. Delaunay, et al., "Glucose-Insulin Kinetics of a Bioartificial Pancrease Made of an AN69 Hydrogel Hollow Fiber Containing Porcine Islets and Implanted in Diabetic Mice", International Society for Artificial Organs, 22(4): pp. 291-299, Blackwell Science, Inc., 1998.

V. Dixit, et al., The Bioartificial Liver: State-of-the-Art, Eur. J. Surg., 1998: Suppl. 582; pp. 71-76.

H. Ohgawara, et al., "Membrane Immunoisolation of a Diffusion Chamber for a Bioartificial Pancreas", International Society for Artificial Organs, 22(9), 1998, pp. 788-794.

S. K. Hunter, et al., "Encapsulated β-islet cells as a bioartificial pancreas to treat insulin-dependent diabetes during pregnancy", Am. J. Obstet. Gynecol, vol. 177, No. 4, pp. 746-752, 1997.

M. R. Pillarella, "Theoretical Analysis of the Effect of Convective Flow on Solute Transport and Insulin Release in a Hollow Fiber Bioartificial Pancreas", Journal of Biomechanical Engineering, May 1990, vol. 112, pp. 220-228.

S. E. Feinberg, et al., "Role of Biomimetics in Reconstruction of the Temporomandibular Joint", Oral and Maxillofacial Surgery Clinics of North America, vol. 12, No. 1, Feb. 2000, pp. 149-160.

N. E. Mukundan, et al., "Oxygen Consumption Rates of Free and Alginate-entrapped βTC3 Mouse Insulinoma Cells", Biomechanical and Biophysical Research Communications, vol. 210, No. 1, May 5, 1995, pp. 113-118.

Y. Tanaka, et al., "Generation of an autologous tissue (matrix) flap by combining and arteriovenous shunt loop with artificial skin in rats: preliminary report", British Journal of Plastic Surgery, (2000), 53, pp. 51-57.

R. Mian, et al., "Formation of New Tissue from an Arteriovenous Loop in the Absence of Added Extracellular Matrix", Tissue Engineering, vol. 6, No. 6, 2000, pp. 595-603.

G. Ahrendt, et al., "Angiogenic Growth Factors: A Review for Tissue Engineering", Tissue Engineering, vol. 4, No. 2, 1998, pp. 117-131.

C. K. Colton, "Engineering challenges in cell-encapsulation technology", Tibtech, May 1996, vol. 14, pp. 158-162.

C. K. Colton, "Bioengineering in Development of the Hybrid Artificial Pancreas", Journal of Biomechanical Engineering, vol. 113, May 1991, pp. 152-170.

R. P. Lanza, et al., "Transplantation of Islet Allografts Using a Diffusion-Based Biohybrid Artificial Pancreas: Long-Term Studies In Diabetic, Pancreatectomized Dogs", Transplantation Proceedings, vol. 25, No. 1, Feb. 1993: pp. 978-980.

C. A. Ramirez, et al., "In Vitro Perfusion of Hybride Artificial Pancreas Devices at Low Flow Rates", ASAIO Journal 1992, pp. M443-M449.

S. Esser, et al., "Vascular Endothelial Growth Factor Induces Endothelial Fenestrations In Vitro", The Journal of Cell Biology, vol. 140, No. 4, Feb. 23, 1998, pp. 947-959.

Y.S. Chang, et al., "Effect of Bascular Endothelial Growth Factor on Cultured Endothelial Cell Monolayer Transport Properties", Microvascular Research 59, pp. 265-277, 2000.

A. Hempel, et al., "Atrial natriuretic peptide clearance receptor participates in modulating endothelial permeability", The American Physiological Society, pp. H1818-H1825, 1998.

T. A. Desi, et al., Microfabricated immunoisolating Biocapsules', Biotechnology and Bioengineering, vol. 57, No. 1, Jan. 5, 1998, pp. 118-120.

T. Murohara, et al., "Transplanted cord blood-derived endothelial precursor cells augment postnatal neovascularization", The Journal of Clinical Investigation, Jun. 2000, vol. 105, No. 11, pp. 1527-1536.

P. Carmeliet, et al., "Mechanism of angiogenesis and arteriogenesis", Nature Medicine, vol. 6, No. 3, Mar. 2000, pp. 389-395.

R. B. Vernon, et al., "A Novel, Quantitative Model for Study of Endothelial Cell Migration and Sprout Formation within Three-Dimensional Collagen Matrices", Microvascular Research 57, pp. 118-133, 1999.

V. Nehls, et al., "The Configuration of Fibrin Clots Determines Capillary Morphogenesis and Endothelial Cell Migration", Microvascular Research 51, pp. 347-364, 1996.

Written Opinion, International Preliminary Examining Authority, Sep. 30, 2004.

A. Trifillis, et al., "Isolation, Culture and Characterization of Human Renal Tubular Cells", The Journal of Urology, vol. 133, Feb., pp. 324-329.

C. Detrisac, et al., "Tissue Culture of Human Kidney Epithelial Cells of Proximal Tubule Origin", Kidney International, vol. 25, 1984, pp. 383-390.

* cited by examiner

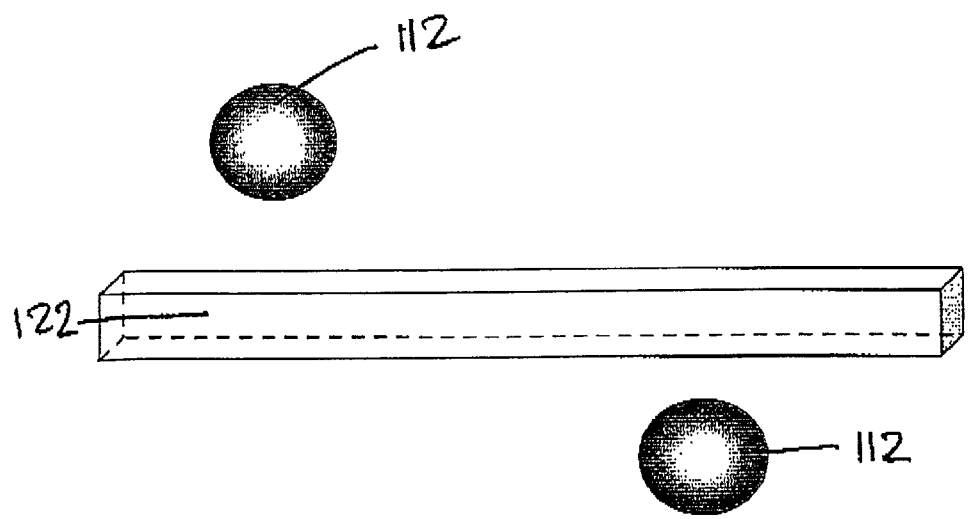
FIG. 2A
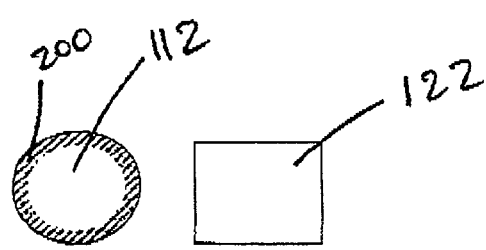 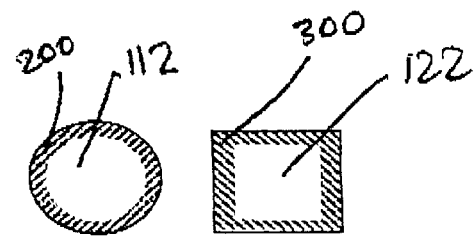
FIG. 2B  FIG. 2C

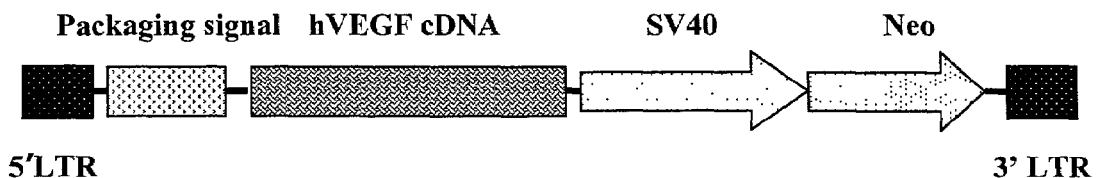

LXSN retroviral vector is derivative of MoMLV. Human $VEGF_{165}$ full length cDNA (995 bp, EcoR I fragment) was inserted into EcoR I site in MCS of LXSN. The expression of human VEGF is controlled by 5' long terminal repeat of MoMLV. Neomycin gene is cloned to the downstream of SV40 promoter as selection marker in mammalian cells. phVEGF.21 plasmid containing human VEGF full length cDNA was from Genentech, Inc.

FIG. 7

DEVICE FOR MAINTAINING VASCULARIZATION NEAR AN IMPLANT

BACKGROUND OF THE INVENTION

1. Field of the Invention

The present invention relates to a device and a method of inducing and maintaining vascularization near an implant for the purpose of facilitating the formation of ultrafiltrate as well as facilitating the transport of oxygen, nutrients and metabolites to/from cells in the implant. More specifically, this invention relates to a device and a method of maintaining vascularization near a bioartificial hemofilter.

2. Discussion of the Background

One traditional approach to development of a bioartificial filtration device is to promote site-directed neovascularization in vivo near a mechanism for removing filtrate (see, for example, J. A. Thompson et al., Science 241, p. 1349-1352, 1988, the contents of which are incorporated herein by reference). In this approach, angiogenic factors (J. Folkman, and Y. Shing, *J Biol. Chem.* 267(16), p. 10931-10934, 1992 the contents of which are incorporated herein by reference) are delivered via exogenous and endogenous routes in order to induce targeted angiogenesis around and among implanted biocompatible hollow fibers. These hollow fibers are envisioned to act as collecting (drainage) conduits of ultrafiltrate produced by the newly-formed capillary network induced by the angiogenic factors. This formulation relies upon the intrinsic properties inherent to all capillary beds that allow them to produce ultrafiltrate when a pressure differential is applied across the capillary bed. This filtrate, or transudate, will collect in the hollow fiber network rather than the usual physiologic sites consisting of the interstitial space and lymphatics. In other words, the vectorial filtrate flow will be from capillary through interstitium into hollow fiber, since the hydraulic pressure difference from capillary lumen to hollow fiber can be greater than 20 mm Hg when the hollow fiber system is connected to an drainage and collection system. Once the filtrate is collected in the hollow fiber network, it can be drawn from the body, thereby mimicking some of the filtration properties of, for example, the kidney.

The inventor has realized that once the administration of angiogenic factors (compounds that spur neovascularization) to such systems is discontinued, the newly formed capillary beds regress from the hollow fibers that collect the ultrafiltrate. Regression decreases blood flow to the hollow fiber network and increases the effective resistance to flow along the path from capillary lumen to hollow fiber. The net result is a decrease in the flow rate of filtrate along this path and a decrease in the clearance of various compounds from the body.

Inducing vascularization in the surroundings is also important in other types of implants. For example, encapsulated cell implants often suffer from a poor supply of nutrients and/or removal of metabolites from the implants themselves. This commonly leads to encapsulated cell necrosis and reduced production of cellular products. The major reason underlying the poor transport characteristics of implants is that, in contrast to normal tissues, typical tissue-engineered implants are characterized primarily by diffussive rather than convective mass transport processes. Even when designers incorporate convective transport (see for example Pillarella and Zydney, *J Biomech Eng* 112(2):220-8, 1990, incorporated herein by reference) by grafting the implant to the vasculature, transport rates are still trailing those of native tissues because the latter possess an extensive microvasular network. By spurring vascularization in and around such implants, however, more facile transport of metabolites and/or nutrients to and from the implants can be achieved.

Furthermore, the inventor has realized that ultrafiltrate formed in a hemofilter such as the vascularized implant described in this invention, may provide a supply of nutrients and oxygen via convective transport to cell implants, while denying access of immunoglobulins, immune cells, and complement proteins to the implanted cells, thereby avoiding the immunologic consequences of blood contact with implanted cells.

SUMMARY OF THE INVENTION

Accordingly, one object of this invention is to provide a novel method and device for inducing and maintaining neovascularization near an implant, and more particularly near a bioartificial filtration device.

Another object of this invention is to provide a novel method and device for minimizing the need to administer angiogenic factors by way of, for example, injection, to a site near an implant, and more, specifically, a site near a bioartificial filtration device.

A further object of this invention is to provide a novel method and device for maintaining secretion of at least one angiogenic factor near an implant and, more specifically, near a bioartificial hemofiltration device.

A still further object of this invention is to provide a novel method and device for maximizing output of other (i.e., non-angiogenic factor) cellular products from an encapsulated cell implant.

A yet further object of this invention is to provide a novel method and device for providing a self-maintaining bioartificial hemofiltration device.

A yet further object of this invention is to provide a novel method and device for delivery of oxygen and nutrients to implanted cells.

A yet further object of this invention is to provide a novel arrangement of surfaces to provide access of cultured cells to convective flow of nutrients.

Another object of this invention is to provide methods of preparing the devices described above.

Another object of this invention is to provide a method of implanting the device described above into a recipient, e.g., a patient.

It is yet another object of the present invention to provide a method of utilizing an ultrafiltrate produced by a filtration device.

These and other objects of the invention may be achieved first by isolating cells such as myoblasts (preferably autologous from the eventual recipient) that can be used to provide at least in part a supply of at least one angiogenic factor to the bioartificial filtration device. If necessary, the isolated cells (preferably myoblasts) can be transfected with a gene for the selected angiogenic factor(s). Regardless of which angiogenic factor is selected, the cells can then be seeded into, for example, encapsulating hollow fibers as needed. Once seeded, the cells can be expanded as necessary, e.g., into the intraluminal space of the encapsulating hollow fibers. In one embodiment, one or more organic components that promote cell growth and/or attachment are provided in the intraluminal space. After seeding and/or expansion, the cells can be converted to differentiated cells (such as converting myoblasts to myotubes) and their growth arrested.

The resulting device would thus supply an implant, such as a bioartificial filtration device, with a supply of angiogenic factors from appropriate cells. This would prevent regression of capillary beds from the device and thereby maintain sufficient clearance therethrough and/or transport of metabolites and/or nutrients to and from the implant. In a preferred embodiment, the cells are myoblasts or myotubes transfected with genes coding for a selected angiogenic factor. The device may also include a fibrin glue layer to facilitate cell attachment.

Ultrafiltrate is collected in the device. In a further embodiment of the invention, the device could include one or more ports through which the generated ultrafiltrate could be directed to the urinary system or to a single transdermal port for collection ex vivo. Alternatively, ultrafiltrate could be directed in vivo to one or more tissue-engineered implants either for further processing, for example by an implantable bioartificial renal tubule, or to improve the mass transport properties of another implant, for example a bioartificial pancreas, or liver. Indeed, a hemofilter, whether synthetic or bioartificial, allowing passage of water, electrolytes, carbohydrates and proteins of low molecular weight, oxygen, and carbon dioxide will allow flux of cell, immunoglobulin, coagulation factor, and complement-free plasma to implanted cells.

Direct access by cells to a stream of nutrients and oxygen may be realized within the confines of a small volume by various microscopic geometries readily achievable through traditional cell immobilization technologies or newer techniques such as micromachining. A preferable micromachined array of plates or posts provides ample surface area for cells to attach as monolayers and each gain access to a nutrient stream flowing through the plates or posts.

Accordingly, the present invention provides an implantable hemofilter device, comprising:

an implant body, and first cells, wherein the first cells produce at least one angiogenic product.

The present invention also provides a method of producing the implantable hemofilter device described above, comprising combining the first cells and the implant body.

The present invention also provides a method of producing an implantable hemofilter device capable of maintaining vascularization when implanted, comprising:

obtaining first cells capable of releasing an angiogenic product; and associating the first cells with an implant body, wherein the first cells are capable of releasing the angiogenic product into a surroundings of implantable hemofilter device after implantation.

The present invention also provides a method of producing a hemofilter implant, comprising:

implanting the implantantable hemofilter device described above in a subject, wherein the angiogenic product produced by the first cells induces the formation of vascular tissue near the implant.

The present invention also provides a method of utilizing an ultrafiltrate produced by a filtration device, comprising:

transferring an ultrafiltrate produced by a fitration device implanted in a subject to a tissue-engineered construct which is also implanted in the subject.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 2A illustrates an exemplary hollow fiber conduit surrounded by one or more encapsulation/entrapment bodies that contain cells that produce angiogenic factor(s);

FIG. 2B illustrates an exemplary cross section of the hollow fiber conduit and an encapsulation/entrapment body of FIG. 2A where the encapsulation/entrapment body contains cells that produce angiogenic factor(s);

FIG. 2C illustrates an exemplary cross section of the hollow fiber conduit and an encapsulation/entrapment body of FIG. 2A, where the encapsulation/entrapment body contains cells that produce angiogenic factor(s) and the hollow fiber conduit contains cells that perform a therapeutic function, e.g., produce another molecular product;

FIG. 7 illustrates an exemplary SN retroviral vector containing human $VEGF_{165}$ cDNA according to one embodiment of the present invention;

DETAILED DESCRIPTION OF THE PREFERRED EMBODIMENTS

Figure 1A:
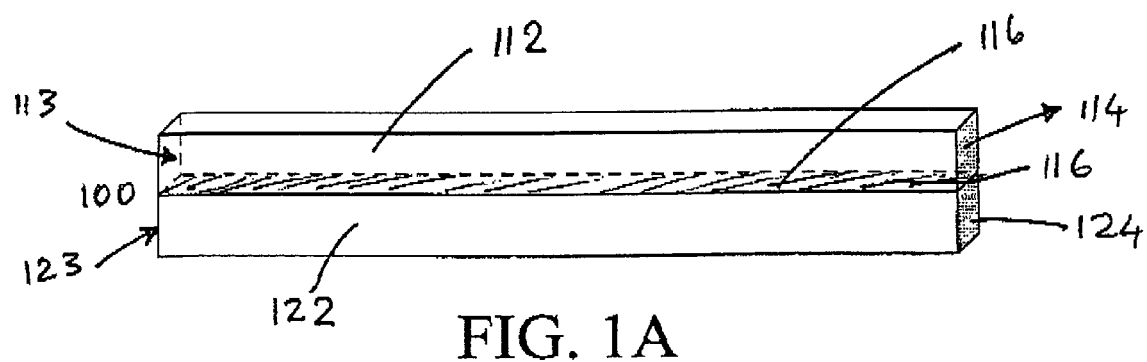
FIG. 1A illustrates an exemplary double hollow fiber.

The implantable hemofiltration device of the present invention is based on the recruitment and maintenance of a vascular network (capillary bed) around a porous conduit arranged in a manner appropriate for collecting ultrafiltrate. This is accomplished by the first cells, which produce at least one angiogenic factor. As used herein, the term "angiogenic factor" refers to a substance that is capable of recruiting and maintaining the vascular network around the implant. The first cells may secrete angiogenic factor(s) continuously. These cells may secrete the factor naturally or may be genetically modified to secrete it.

The first cells are immobilized on an appropriate support structure (scaffold). The first cells may be on the outside of solid or hollow support elements such as fibers, spheres, etc. These cells may be on the inside of hollow or substantially hollow structures such as hollow fibers, capsules, or gels, if these structures are permeable to nutrients and cellular products, in particular the angiogenic products. In one embodiment, the first cells may be on the exterior of the implant body.

In one specific embodiment, the implant body comprises a porous encapsulation or entrapment body. In another embodiment, the porous encapsulation body is in the form of a tube.

The implant body may comprise one or more of the following materials: glasses, metals, ceramics, and polymers. Examples of polymers include the following: polypropylenes, polysulfones, cellulosic polymers, cellulose actetates, rayons, polyacrylonitriles, polymethylmethacrylates, polycarbonates, polyfluoroethylenes, alginates, and chitosans.

The arrangement of the first cells on the support structure results in a capillary bed forming throughout the implant. Blood flowing through this capillary bed brings nutrients and oxygen to feed the first cells so they continue secreting the angiogenic factor(s). A steady-state vascularized network will form as a result. The secreted angiogenic factors may also be used to regulate the permeability (leakiness) of the capillary bed.

Hollow fibers (tiny thread-like tubes) with permeable walls may be arranged to span the whole space of the implant and are connected together to a common conduit or outlet. This makes up the implant's ultrafiltrate collection network. These hollow fibers are surrounded by the support structure containing the first cells and after implantation and recruitment of blood vessels, by the capillary bed. Some blood filters through the capillary bed and is picked up by the ultrafiltrate collection network. The ultrafiltrate may be taken outside the body through a transdermal port. The ultrafiltrate may be directed to a body cavity, such as the bladder.

The implant may also contain cells in addition to the first cells which produce the angiogenic product. In fact, it is contemplated that the implant of present invention may contain a wide variety of different cell types, each contributing a function which contributes to the overall effectiveness of the implant. Hereinafter referred to as "second cells," these cells may perform a therapeutically useful function, such as producing a therapeutcally useful substance. As used herein, the term "therapeutcally useful substance" refers to a material which has a beneficial effect on the recipient after the device of the present invention is implanted. One specific example of a therapeutically useful substance is a hormone.

Alternatively, the second cells may have metabolic activity. As used herein, the term "metabolic activity" means that the cells may catabolize, break down, or convert a substance. Examples of such cells include liver cells and proximal tubule cells.

The implant may also be used to act as a bioartificial glomerulus. In this embodiment, the implant is used as an alternative or supplement to dialysis treatment for individuals suffering from chronic renal disease. The implantable hemofilter device may also be associated with other cells which perform a beneficial action on the recipient. Such beneficial action includes producing therapeutic molecules useful to the recipient. These useful molecules may be hormones, such as insulin. The implant may function both as an implantable bioartificial glomerulus and as an additional therapeutic device, e.g., producing insulin, or function only in this second capacity. Other cells may also be incorporated into the device, such as cells to support adhesion, growth, and/or differentiation. These cells may also have metabolic or secretory activity, i.e., produce nutrients for the living matter associated with the implant.

Such a device may be constructed as follows: the first cells may be combined with other cells (second cells) in a single implant, e.g., two hollow fiber groups where one supports the first cells and the other collects the ultrafiltrate and supports the second cells. Alternatively, two different implant components may be used where the ultrafiltrate is directed from the outlet of the hemofilter to the second implant to provide nutrients. After going through the second implant, the ultrafiltrate may be discarded (directly through a transdermal port or indirectly by being sent to a body cavity, such as the bladder) or could be reconditioned and reused in part or in whole, e.g., directed to the peritoneal cavity or returned to the vein. The present invention also provides a method of utilizing an ultrafiltrate produced by a filtration device to provide nutrients and immunoprotection to cellular implants. The ultrafiltrate may be provided by the implantable hemofilter device described above. Alternatively, the ultrafiltrate may be provided by any hemofilter, including fully inanimate ones, i.e., hemofilters that do not contain cells unlike those embodiments described above.

The implantable device of the present invention may be implanted in any suitable location in the recipient. For example, the device may be implanted subcutaneously and/or peritoneally. Alternatively, the device may be implanted retroperitoneally. For example, when implanted retroperitoneally the device may be associated with the old/scarred kidney by being implanted in the space formerly occupied by the diseased tissue. This approach may be advantageous as it enables implantation in a site privileged by the presence of extensive vascularization and ultrafiltrate collection networks.

In a further embodiment of the invention, the hemofilter device may be connected to a second implant in the recipient. When the second implant contains the second cells that provide a therapeutic function, those cells are nourished by the hemofilter-generated ultrafiltrate.

The recipient may be a human or a non-human animal. Preferred non-human animals are mammals. Examples include dogs, cats, cows, horses, pigs, etc.

Referring now to the drawings, wherein like reference numerals designate identical or corresponding parts throughout the several views, and more particularly to FIG. 1A thereof, wherein a single, illustrative example of a permeable double hollow fiber 100 for use in a bioartificial filtration device according to the present invention is illustrated. The permeable hollow fiber 100 has two cavities, namely encapsulation/entrapment body 112 and conduit 122 in direct fluid communication with one another at least indirectly through the surroundings (not shown), and potentially through the permeable wall 116 as well. These surroundings can include, for example, tissue whose vascularization is maintained by angiogenic factors produced in fiber cavity 112. As illustrated, the encapsulation/entrapment body 112 of permeable hollow fiber 100 is rectangular volume, as is the conduit 122. Furthermore, the illustrated exemplary encapsulation/entrapment body 112 and conduit 122 are contiguous with one another. Naturally, the encapsulation/entrapment body 112 and conduit 122 need not have this geometry or be contiguous. Indeed, several alternate geometries are in fact preferable when considered independent of the constraints of ease and feasibility of manufacturing and implantation. For example, the contact area 116 could be made impermeable, or encapsulation/entrapment body 112 could be in the form of a cylinder located a predetermined distance away from conduit 122. Another potential geometry would include arranging encapsulation/entrapment body 112 and conduit 122 neighboring or in contact with one another in a helical geometry. It is desirable that an appropriate separation distance between encapsulation/entrapment body 112 and conduit 122 be maintained so that angiogenic factors produced in encapsulation/entrapment body 112 promote or maintain vascularization in the neighborhood of conduit 122 and thereby maximize the net flow of filtrate therethrough.

Both the encapsulation/entrapment body 112 and the conduit 122 contain surfaces 113 and 114, and 123 and 124, respectively that can be open or capped. Each surface 113, 114, 123 and/or 124 can be "capped" by simple extension of permeable membrane material of permeable hollow fiber 100 to cover these surfaces (in which case these surfaces would be essentially indistinguishable from the remainder of the permeable membrane), or they can be capped by another body that is, for example, pressure fitted into an open surface 113, 114, 123 and/or 124. In a preferred embodiment, conduit 122 contains a surface 123 that remains uncovered by a permeable membrane and is in fluid communication with other surfaces 123 of other conduits 122, as illustrated, for example, in FIGS. 4A and 4B.

The permeable hollow fiber 100 can be formed of any material that is permeable to water and capable of supporting cell growth and/or attachment. Typically, the ultrafiltration coefficient of the permeable hollow fiber 100 is greater than 20 mL/hr,Torr,m$^2$, and preferably between 20 and 100 mL/hr,Torr,m$^2$. A permeable hollow fiber 100 suitably has a molecular weight cutoff which is less than or substantially equal to 60,000 g/mole. Examples of such polymers include various polyproylenes, polysulfones, cellulosic polymers including cellulose acetate, rayons, polyacrylonitriles, polymethylmethacrylates, polycarbonates, polyfluoroethylenes, and various copolymers thereof and other polymeric species. It is important to note that the permeability of body 112 and conduit 122 may be the same or different from each other.

The internal and/or external surface(s) of the permeable hollow fiber 100 is, in some embodiments, coated with organic components (not shown) to promote cellular growth and/or adhesion thereon and/or therein. These organic components can include traditional extracellular matrix components such as Type I collagen, Type IV collagen, laminin, Matrigel, various proteoglycans such as heparin sulfate and dermatan sulfate, fibronectin, and combinations thereof. Other potential organic components include engineered components such as Pronectin-F, a recombinant protein containing multiple copies of the RGD cell attachment ligand of human fibronectin interspersed between repeated structural peptide segments derived from spider silk, thereby providing a non-degradable highly stable substrate for cell attachment. In a preferred embodiment, fibrin glue can serve as an organic component for promoting cellular growth and/or adhesion. Fibrin glue is the natural complex that promotes wound healing in vivo. Furthermore, the angiogenic potential of epithelial cells is critically dependent upon both soluble and insoluble factors. Soluble factors include growth factors. Insoluble factors include complex extracellular matrices, such as collagen gels, or purified extracellular matrix molecules, including laminin, fibronectin, collagen types I and IV, which are contained in fibrin glue. Finally, fibrin glue can be easily generated as autologous material from the recipient.

Various chemistries for coating permeable hollow fiber 100 with organic components are known in the art and dependent upon the chemical nature of permeable hollow fiber 100. These chemistries range from non-specific adsorption and photo cross-linking of the organic components to permeable hollow fiber 100 to specific and even regiospecific immobilization schemes such as reductive amination and those disclosed in, for example, U.S. Pat. Nos. 5,858,653, 4,973,493, 5,002,582, 5,414,075, and 5,580,697, the contents of all of which are incorporated herein by reference.

Figure 1B:
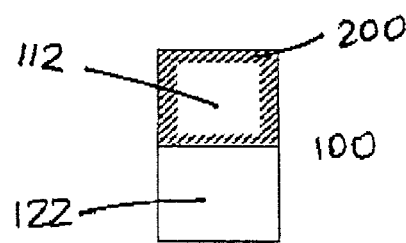
FIG. 1B illustrates an exemplary cross section of one embodiment of the double hollow fiber of FIG. 1A that contains cells that produce angiogenic factor(s) in one of the two hollow fibers.
Figure 1C:
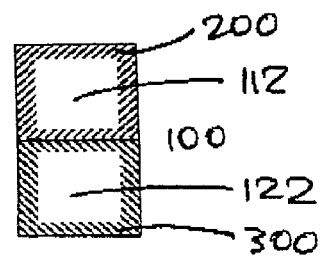
FIG. 1C illustrates an exemplary cross section of a second embodiment of the double hollow fiber of FIG. 1 that contains both cells that produce angiogenic factor(s) in one hollow fiber and cells that perform a therapeutic function, e.g., produce another molecular product, in a second hollow fiber.

As illustrated in the exemplary cross-sections of hollow fiber 100 illustrated in FIGS. 1B and 1C, the encapsulation/entrapment body 112 and conduit 122 do not necessarily contain the same constituents. In both illustrated embodiments, cells 200 capable of providing a supply of at least one angiogenic factor can be located in encapsulation/entrapment body 112 of permeable hollow fiber 100. The supply of angiogenic factor(s) from the encapsulation/entrapment body 112 will promote neovascularization around an implanted hollow fiber 100 and inhibit regression once a steady state is reached or external administration of angiogenic factor(s) is curtailed. Illustrated cells 200 are shown lining the lumen of encapsulation/entrapment body 112. It is known in the art that, excepting cavities of the smallest diameters, cells entrapped and/or encased in cavities defined by semi-permeable membranes are easiest to maintain near the surface(s) of those cavities. This is presumably due to mass transport across the semipermeable membrane being most facile near the surfaces of those cavities. Regardless of the origins of this effect, it is acknowledged that the cellular population of encapsulation/entrapment body 112 would ideally be distributed throughout encapsulation/entrapment body 112, although the distribution is otherwise illustrated in the figures.

As illustrated in FIG. 1B, the conduit 122 can remain substantially clear of cells and cellular products. In one embodiment, conduit 122 will serve to conduct any filtrate away from the vascularization induced or maintained by cells 200 of encapsulation/entrapment body 112. This will be done through an open surface 123 of conduit 122, to be discussed further in regard to FIGS. 4A and 4B.

As illustrated in FIG. 1C, conduit 122 can also contain a cell population 300. Cell population 300 can be selected to provide any of a number of cellular products to the surroundings of conduit 122. Examples of cell population 300 include but are not limited to stem cells, hematopoietic stem cells, hepatocytes, and pancreatic islet cells. The desirability, use, and procedures for encapsulating such cell populations 300 have been described, for example, in U.S. Pat. Nos. 5,639,275, 5,656,481, 5,550,050, 5,653,975, 5,676,943, 5,773,286, 5,795,790, the contents of all of which are incorporated herein by reference.

FIG. 2A illustrates an exemplary permeable hollow fiber conduit 122 surrounded by one or more spherical encapsulation/entrapment bodies 112 that contain cells that produce angiogenic factor(s). As described in regard to FIG. 1A, the geometry of the encapsulation/entrapment bodies 112 is arbitrary, as explicitly illustrated by the spherical encapsulation/entrapment bodies 112 of this illustration. Likewise, the placement of the encapsulation/entrapment bodies 112 relative to the conduit 122 only requires that cellular products released from encapsulation/entrapment bodies 112 are able to induce and/or maintain vascularization in the vicinity of conduit 122. The separation distance between encapsulation/entrapment bodies 112 and conduit 122 will depend upon several factors, including but not limited to the permeability of membranes that form encapsulation/entrapment bodies 112 and conduit 122, the tissue into which encapsulation/entrapment bodies 112 and conduit 122 are implanted, and the transport, angiogenicity, and/or other properties of the angiogenic factor produced by cells 200 in encapsulation/entrapment bodies 112. For the purposes of this invention, encapsulation/entrapment bodies 112 are preferably within 10 mm of conduit 122, and more preferably within 1 mm.

FIG. 2B illustrates a situation analogous to FIG. 1B wherein encapsulation/entrapment bodies 112 contain cells 200 that produce the at least one angiogenic factor and conduit 122 remains substantially clear of cells and cellular products.

Likewise, FIG. 2C illustrates a situation analogous to FIG. 1C, wherein encapsulation/entrapment bodies 112 contain cells 200 that produce the at least one angiogenic factor and conduit 122 contains a cell population 300 that is selected to provide any of a number of cellular products to the surroundings of conduit 122.

Figure 3A:
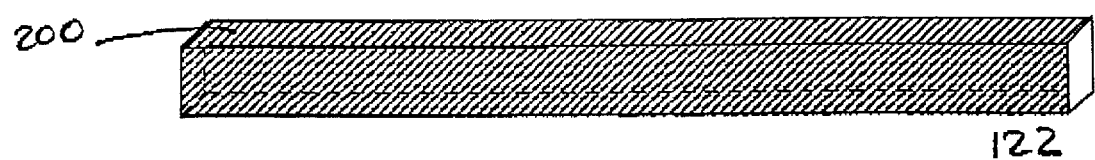
FIG. 3A illustrates an exemplary hollow fiber conduit surrounded by cells that produce angiogenic factor(s)

FIG. 3A illustrates the situation wherein cells 200 that produce the at least one angiogenic factor are immobilized external to conduit 122 and the encapsulation/entrapment body 112 is dispensed with entirely. This embodiment may favor autologous cells 200 that produce the at least one angiogenic factor. In this case, organic components that promote cellular growth and/or adhesion, such as fibrin glue, are disposed on the external surface of conduit 122 for immobilization of cells 200. In the case where cells 200 are not autologous, they can be immunoprotected, e.g., by coating with an appropriate semipermeable membrane.

Figure 3B:
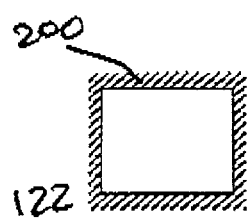
FIG. 3B illustrates an exemplary cross section of the hollow fiber conduit of FIG. 3A surrounded by cells that produce angiogenic factor(s)

FIG. 3B illustrates a situation analogous to FIGS. 1B and 2B wherein conduit 122 remains substantially clear of cells and cellular products.

Figure 3C:
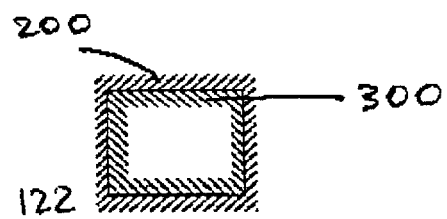
FIG. 3C illustrates an exemplary cross section of the hollow fiber conduit of FIG. 3A surrounded by cells that produce angiogenic factor(s) and containing cells that perform a therapeutic function, e.g., cells that produce another molecular product.

Likewise, FIG. 3C illustrates a situation analogous to FIGS. 1C and 2C, wherein conduit 122 contains a cell population 300 that is selected to provide any of a number of cellular products to the surroundings of conduit 122.

Figure 4A:
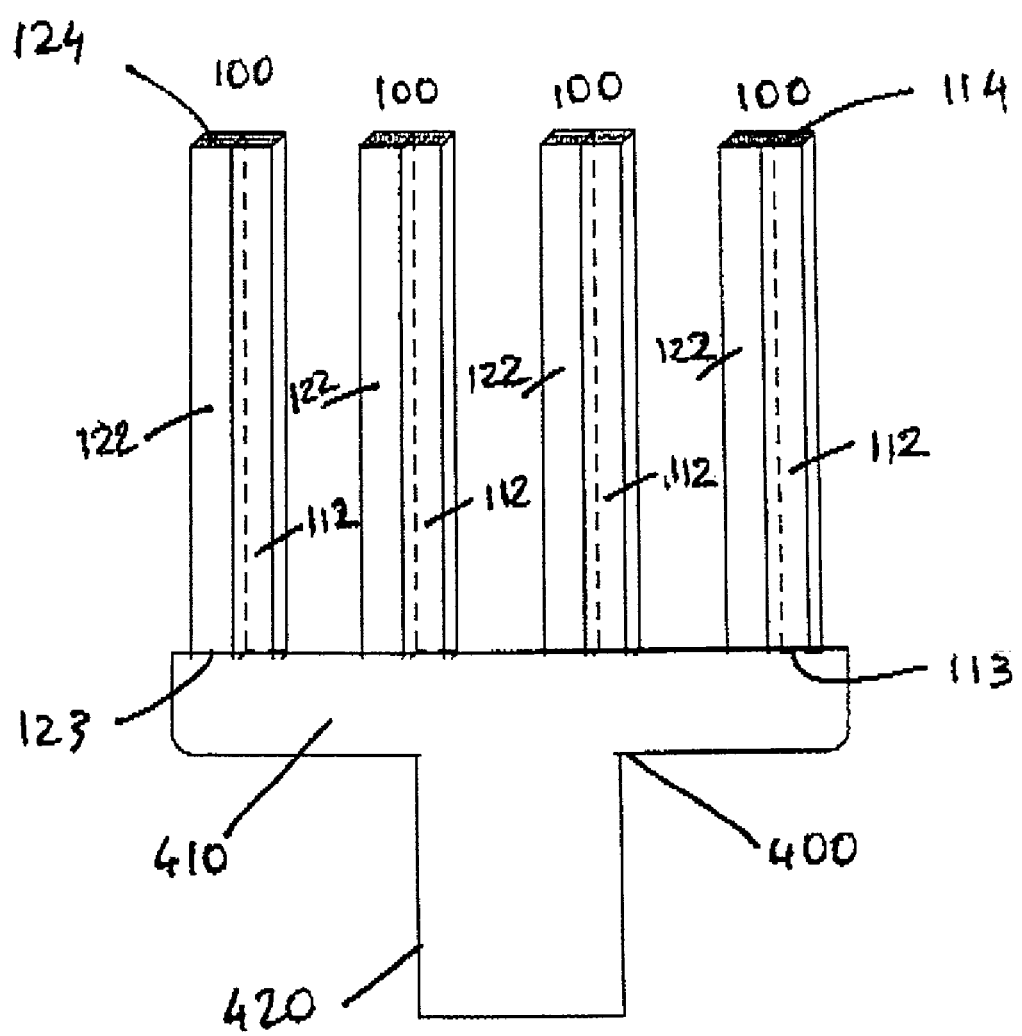
FIG. 4A illustrates an exemplary arrangement of plural double hollow fibers of FIG. 1A arranged for implantation wherein plural hollow fiber conduits are in fluid communication with one another by way of a manifold that connects to a manifold outlet port.
Figure 4B:
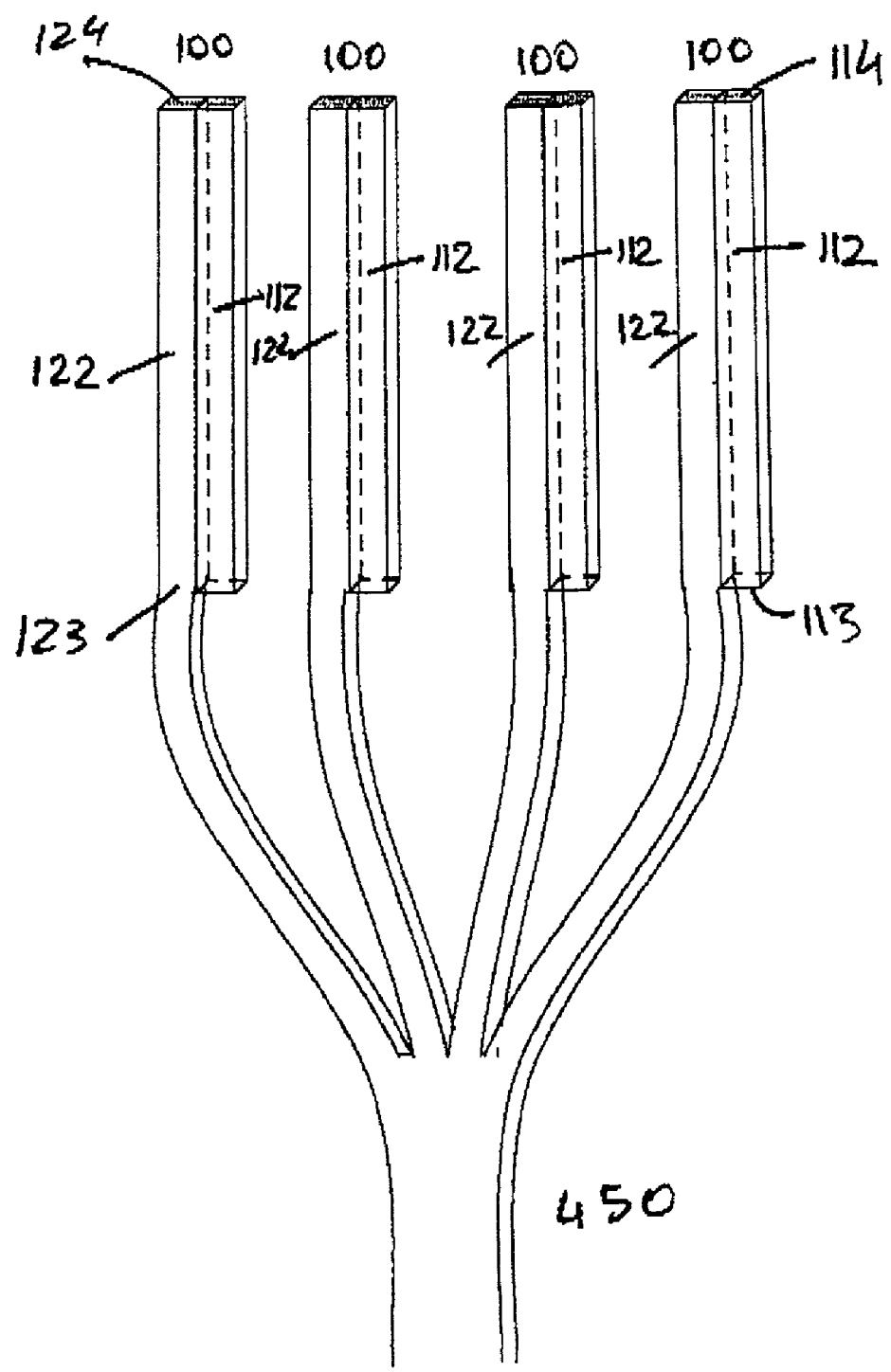
FIG. 4B illustrates an exemplary arrangement of plural double hollow fibers of FIG. 1A arranged for implantation wherein plural hollow fiber conduits are in fluid communication with one another and join at a common outlet.

FIG. 4A illustrates an exemplary connection of several permeable double hollow fiber 100 substantially in parallel to a manifold 400 in one embodiment suitable for a bioartificial filtration device. Although FIG. 4A and FIG. 4B are illustrated using the exemplary double hollow fiber of FIG. 1A, many other embodiments thereof, such as those illustrated in FIGS. 2A and 3A, can be connected to an analogous manifold 400. Furthermore, although several conduits 122 are in fluid communication with one another by way of manifold 400 in FIGS. 4A and 4B, it is not necessary that this be the case. For example, a surface 123 of a conduit 122 can simply be capped leaving conduit 122 to act simply as an encapsulating membrane of any geometry.

Manifold 400 contains a channel 410 that places a plurality of conduits 122 of permeable double hollow fibers 100 in fluid communication with one another and a manifold port 420 by way of a plurality of open surfaces 123. Manifold 400 furthermore serves to maintain a desirable spacing between the permeable double hollow fibers 100. In the common case where the permeable double hollow fibers 100 are flexible, an opposite manifold (not shown) can be placed on ends 124 of permeable double hollow fibers 100. In one embodiment, this opposite manifold can serve to cap the open portions 124 of conduits 122 or the open portions 114 of encapsulation/entrapment bodies 112. The opposite manifold may also provide a means for seeding first cells into conduit 112 during preparation of the device. Likewise, if necessary, manifold 400 can cap an open portion 113 of encapsulation/entrapment bodies 112.

In embodiments wherein the bioartificial filtration device has been implanted, the manifold port 420 can be in fluid communication intracorporeally with other natural or bioartificial tissues, or extracorporeally with a transdermal port for removal of filtrate from the body.

FIG. 4B illustrates an exemplary arrangement of plural double hollow fibers of FIG. 1A arranged for implantation wherein plural hollow fiber conduits are in fluid communication with one another and join at a common outlet 450. In the illustrated embodiment, each of the surfaces 113, 114, and 124 are capped either by the membrane material itself or by a third material that is, for example pressure fitted, in one or more open surfaces 113, 114, and 124. However, the open surfaces 123 are part of the path that joins the plural hollow fiber conduits. Once again, when the permeable double hollow fibers 100 are flexible, an opposite manifold (not shown) can be used to maintain proper spacing thereof and/or cap the open portions 124 of conduits 122 or the open portions 114 of encapsulation/entrapment bodies 112.

In embodiments wherein the bioartificial filtration device has been implanted, the common outlet 450 can be in fluid communication intracorporeally with other natural or bioartificial tissues, or extracorporeally with a transdermal port for removal of filtrate from the body.

Figure 5A:
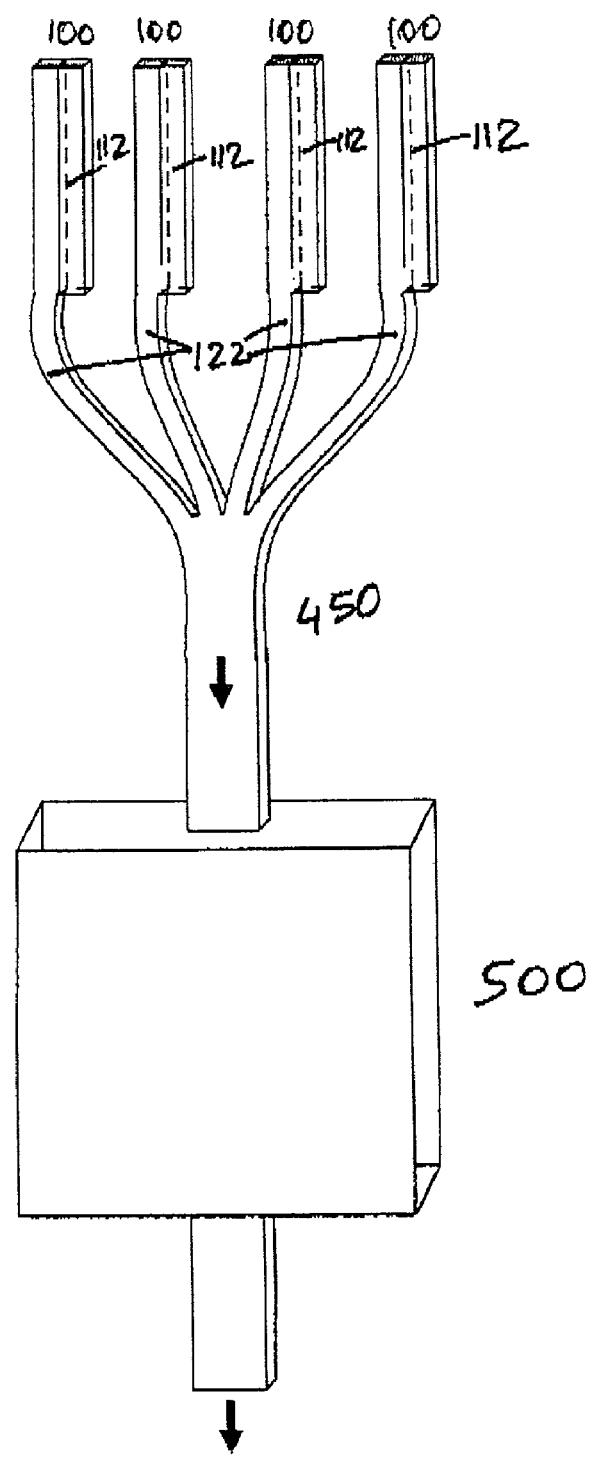
FIG. 5A illustrates an exemplary hemofilter unit, such as that shown in FIG. 4B, arranged in series with a second implant containing cells that either process the ultrafiltrate or utilize it as their primary source of oxygen and nutrients as well as vehicle for product delivery.

Manifold 400 or outlet 450 of the hemofilter may be connected through a conduit to flow into natural or artificial tissues in the body, as depicted schematically in FIG. 5A. For example, it could drain into the urinary tract so that ultrafiltrate generated to supplement renal filtration is collected and dispensed together with urine. Moreover, prior to draining the ultrafiltrate may be directed to additional bioartificial tissues for further processing, for example as in the case of a bioartificial tubule connected to the hemofilter in series to provide the first realistic bioartificial kidney, or to facilitate the oxygen and nutritional requirements of tissue-engineered implants, for example, a bioartificial pancreas or liver.

FIG. 5A illustrates an exemplary arrangement of hollow fibers and conduit to tissue-engineered construct 500, essentially an implantable bioreactor containing cells such as hepatocytes, insulin secreting cells, or proximal tubule cells: In the illustrated embodiment, ultrafiltrate formed by vascularized hollow fibers is directed via the visualized conduit to the bioreactor 500; from there it may be further directed to the central circulation, to the urinary system, or to a transdermal port for extracorporeal collection and dispensing.

In one embodiment, cells immobilized in the bioreactor are capable of producing insulin in response to glucose homeostasis, for example pancreatic islets or insulinomas such as members of the βTC or MIN lines. The practicality and advantage of convective flow of ultrafiltrate to these-cells-may be-better appreciated by a quantitative description of the metabolic needs of these cells and the supply afforded by an stream of ultrafiltrate. In this example, insulin-secreting cells derived from pancreatic tissue are used for calculations, but the novelty and usefulness of this invention is in no way limited to these cells.

The insulinomas when grown in culture consume one μmol of oxygen per minute per $10^9$ cells (Mukundan et al., Biochem Biophys Res Commun. 210(1):113-8, 1997) media and occupy in the order of 100 square microns or $1\times10^{-10}$ m$^2$/cell, and. The cell number needed to synthesize enough insulin to supply the needs of an adult human is estimated to be in the order of $2\times10^9$ cells. Therefore, the oxygenation requirements of a bioreactor 500 containing these cells is approximately 2 μmol/min. Since cell-free ultrafiltrate does not carry hemoglobin its oxygen content is determined by the $O_2$ partial pressure of filtered blood. In clinical practice blood oxygenation typically exceeds 50 mmHg; this value translates to an ultrafiltrate oxygen content of 774 μmol/L. Thus, under ideal conditions the volume of ultrafiltrate required to supply the oxygenation requirements of bioreactor 500 containing insulin-secreting cells is only 2.58 ml/min.

By the above calculations the inventors have realized the practicability, novelty, and advantage of this method of supplying nutrition and oxygen to implanted cells. Furthermore, the inventor has realized that the difficulty of maintaining viability of cellular elements in an implantable bioreactor is exacerbated by the need to protect cells within the bioreactor from cellular and immunologic elements within the bloodstream. This has in the past been addressed by means of a semipermeable membrane surrounded by blood or interstitial fluid and through which nutrients and oxygen diffuse by passive transport down their respective concentration gradients. Waste products from the cells diffuse away from the bioreactor in a similar fashion. Typical arrangements are described in S. K. Hunter et al., Am. J. Obstet Gynecol 1997; 177:746-52, H. Ohgawara et al., Artif Organs 1998; 22:788-794, H. Hayashi et al., Transplantation Proceedings 1996; 28:1428, R. Calafiore et al., Transplantation Proceedings 1996; 28:812-813, C. Delaunay et al., Artif Organs 1998; 22:291-299, K. Naruse et al., ArtifOrgans 1998; 22:1031-1037, B. Busse et al., Ann NY Acad Sci 1999; 875:326-39, and V. Dixit et al., Eur J Surg 1998; Suppl 582:71-76, the contents and disclosure of which are incorporated hereinby reference. The supply of nutrients and oxygen by convective flow of cell-free ultrafiltrate alleviates the requirement for a barrier across which nutrients and oxygen must diffuse. The inventor has realized that it is advantageous to arrange cellular elements in a implantable bioreactor so that each has access to the convective flow and so that a minimum of volume is used. The inventor has realized that these conditions may be achieved through available technologies such as the use of hollow fiber modules or the use of micromachining to create constructs characterized by large surface areas within a small volume. In particular, the practicality and advantage of such micromachined constructs made of silicon or other materials may be more readily appreciated by the discussion below.

Figure 5B:
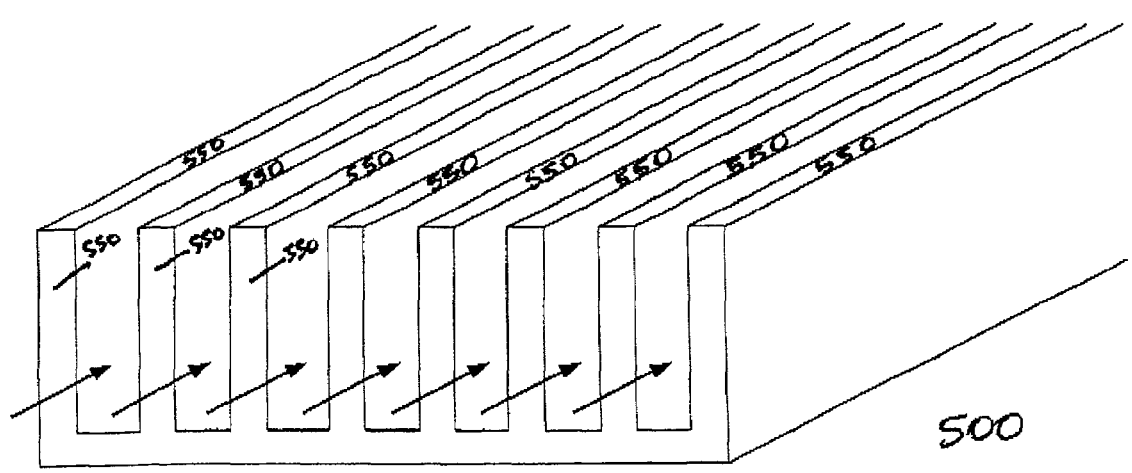
FIG. 5B illustrates an exemplary detailed view of the second implant depicted in FIG. 5A whereby a parallel plate array provides a high-surface-to-volume ratio for the adhesion of anchorage-dependent cells.

FIG. 5B illustrates an exemplary bioreactor 500 comprising micromachined parallel plates 550 whereupon anchorage-depended cells may be grown. In the preferred embodiments cells may be autologous, allo-, iso-, or xeno-transplanted mammalian cells, which may or may not have been modified to produce or absorb previously specified substances. The machining of small structures with high aspect rations by surface or bulk micromachining is well known and understood in the art, as described in J Voldman et al., Annu. Rev. Biomed. Eng. 1999; 1:401-425, the contents of which are incorporated herein by reference. In the preferred embodiments these parallel plates may be machined from any of, but in no way limited to, silicon, polyamide, silicon dioxide, or silicon nitride. It is understood that to effect and facilitate the attachment of cultured cells to the above-described bioreactor, various chemicals, including but in no way limited to poly-L-lysine, fibronectin, laminin, collagen. The use of these and other chemicals to facilitate attachment of organic chemicals to substrates is well understood in the art, as described in *Principles of Tissue Engineering* by Lanza et al.(eds.), 2nd ed., Academic Press, San Diego, Calif., 2000, the contents of which are incorporated herein by reference.

Assuming the array in FIG. 5B is 6 cm long and comprises of plates 500 μm high, 50 μm thick and spaced apart 20 μm, the surface area available for cell attachment is $6\times10^{-5}$ m$^2$ per plate. Thus, accommodation of $2\times10^9$ cells of 100 μm$^2$ footprint each requires $8.3\times10^3$ plates. The total footprint occupied by such an array is 340 cm$^2$. Equivalently, 50 arrays of 6.8 cm$^2$ each could be used, yielding an overall volume of less than 3.39 ml, a very small volume.

Figure 6:
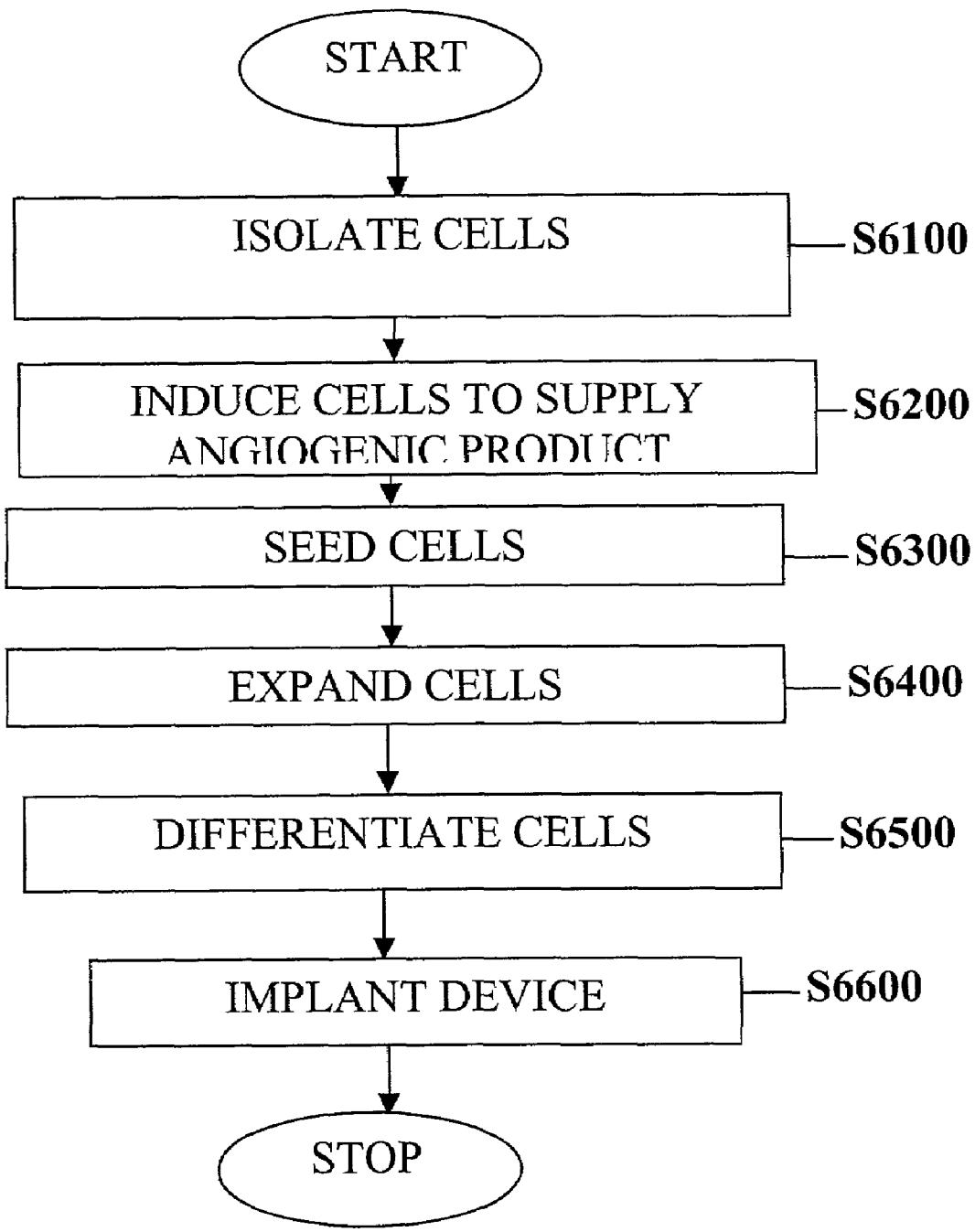
FIG. 6 illustrates an exemplary process flow according to one embodiment of the invention for producing, for example, the embodiments illustrated in FIGS. 1B, 2B, and 3B.

FIG. 6 illustrates an exemplary process flow according to one embodiment of the invention suitable for producing, for example, the embodiments illustrated in FIGS. 1B, 2B, and 3B. In step S6100, a cell capable of producing or being engineered to produce at least one angiogenic factor is isolated. There are several potential cell types capable of supplying or being made to supply at least one angiogenic factor, but a preferred embodiment of this invention involves isolating and then engineering myoblasts to provide quantities of angiogenic factor(s).

In one embodiment, myoblasts are isolated as follows. Fresh human muscle tissue free of visible connective tissues (0.1 to 0.5 g) is washed three times in PBS+AA (Gibco Corp.), minced into about 1-2 mm$^3$ pieces, and digested for 20 min in 35-40 ml of enzymatic cocktail (Collegenase type II 0.1%; Trypsin 0.025%; Dispase 1 unit/ml), at 37° C. with gentle shaking. After digestion, the tissue fragments are pelleted by a mild centrifugation (e.g., 2 min at 100 RPM). The supernatant is then transfered to new tube and trypsin inhibitor (0.25 mg/ml in PBS)is added, and the resulting solution is stored on ice. Cells in the supernatant are then collected by centrifuigation at 500 g for 10 min. The resulting cell pellet is resuspended in MCDB 131 and then spun down at 800 g for 5 min. Once again, the cell pellet is resuspended in MCDB 131 and then spun down at 800 g for 5 min. Next, the cell pellet is suspended in 5 ml Skeletal Myoblast Growing Medium (EGF 5 ug/500 ml; Insulin 50 mg/500 ml; BSA 250 mg/500 ml; Fetuin 250 mg/500 ml; Dexamethasone 0.2 mg/500 ml; AA (Gibco) 5 ml/500 ml)

and the total cell number is determined by cell counting. The cells are then placed on a gelatin-coated 25 mm T-flask (T-25 flask) and incubated at 37° C. for between 1 and 1.5 hours. The medium containing unattached cells is then replaced with fresh skeletal myoblast growing medium, as it is every three days henceforth until the cells are 80% confluent. This usually requires about 3 weeks. Commonly, 95% of the cells isolated using this process are myoblasts. If necessary, the cells can be further purified through cell sorting by using fibroblast specific monoclonal antibody.

Myoblasts can also be isolated, for example, from fetal tissue, or induced from stem cells produced ex vivo using commercially available equipment, such as the AASTROM-REPLICELL system, described in U.S. Pat. Nos. 5,437,994, 5,605,822, 5,763,266, and 5,459,069, the contents of all of which are incorporated herein by reference, using techniques described in U.S. Pat. No. 5,733,727, the contents of which are also incorporated by reference.

An alternate method of isolating myoblasts is described in U.S. Pat. No. 5,919,449, the contents of which are incorporated by reference.

In step S6200, the isolated cells are made to supply the angiogenic factor. This can proceed, for example, by transducing the isolated cells to secrete angiogenic factor(s). Any type of vector may be used, both viral and non-viral. Viral vectors include adenoviral, adeno-associated, retroviral, and lentiviral vectors. In one embodiment, the LXSN retroviral vector which is derivative of MoMLV can be used. Human $VEGF_{165}$ fall length cDNA (995 bp, EcoR I fragment) can be inserted into EcoR I site in MCS of LXSN. The expression of human VEGF can be controlled by 5' long terminal repeat of MoMLV. The neomycin gene can be cloned to the downstream of SV40 promoter as selection marker in mammalian cells. phVEGF.21 plasmid containing human VEGF full length cDNA is available from Genentech, Inc. and illustrated in FIG. 7. The plasmid $LhVEGF_{165}SN$ can be transfected into the amphotropic cell line PA317 by overnight incubation with DOTAP liposomal transfection reagent (Boehringer Mannheim). Resistant clones can be selected in G418 (1 mg/ml), and final clones chosen on the basis of high virus titer and production of hVEGF. The highest titer amphotropic producer (approximately $1 \times 10^6$ colony-forming units/ml) can be used for human myoblast infection. Primary cultured human myoblast cells of 50% confluence can be subjected up to six rounds of transduction with the above-described recombinant virus. Each T-25 flask can be exposed to 5 ml of virus-containing serum-free myoblast growth medium in the presence of polybrene at 8 µg/ml. After final infection, the cells can be split at the ratio of 1 to 3 and selected in G418 of 500 µg/ml. The G418 resistant myoblast cells can be propagated in serum free myoblast growth medium. The human VEGF antigen can be determined by ELISA, and its functions determined by in vitro angiogenic assay. This process results in hVEGF production rate of approximately 500-1000 ng/$10^6$ cells/day.

An alternate method of transfecting myoblasts involving IM injection of naked plasmid DNA encoding a 165-amino acid isoform of VEGF has been described by Y. Tsurumi et al. in *Basic Science Reports* 94, p. 3281-3290, 1996, the contents of which are incorporated herein by reference. Briefly, complementary DNA clones for recombinant human $VEGF_{165}$, can be isolated from cDNA libraries prepared from HL-60 leukemia cells and assembled into a eukaryotic expression plasmid that uses the 736-bp CMV promoter/enhancer to drive VEGF expression. A SV40 polyadenylation sequence can be located downstream from the VEGF cDNA. In some embodiments, included in the plasmid can be a fragment containing the SV40 origin of replication that includes the 72-bp repeat, but this sequence is not functionally relevant (for autonomous replication) in the absence of SV40 T antigen. These fragments occur in the pUC18 vector, which includes an *Escherichia coli* origin of replication and the β-lactamase gene for ampicillin resistance. The biological activity of VEGF secreted from cells transfected with this construct ($phVEGF_{165}$) can be confirmed by evidence that media conditioned by transfected human 293 cells promotes the proliferation of capillary endothelial cells.

Another alternate method of transfecting myoblasts using an adenovirus (Ad) vector encoding for vascular endothelial growth factor 121 cDNA ($Ad_{GV}$ VEGF121.10) has been described by S. R. Patel et al. in Human Gene Therapy 10, p. 1331-1348, 1999, the contents of which are incorporated herein by reference.

Yet another method of transfecting myoblasts is described in U.S. Pat. No. 5,733,727, the contents of which are incorporated by reference.

In a preferred embodiment, the angiogenic factor produced by the transduced myoblasts is $VEGF_{165}$. The grounds for this are severalfold. For example, the human VEGF gene has been used in vivo in several mammalian models for angiogenesis with no immunogeneic response reported. Furthermore, VEGF has been shown to be highly specific, for its receptors are localized almost exclusively in vascular endothelial cells. Naturally, other angiogenic growth factors can be used with the present invention and include other isoforms of vascular endothelial growth factor (VEGF), angiopoietins, fibroblast growth factors (FGF). VEGF is the preferred factor due to its specificity of action on endothelium and its ability to increase vascular permeability. The human VEGF gene is organized into 8 exons and alternative exon splicing results in the generation of four different molecular species of 121, 165, 189 and 206 amino acids. $VEGF_{165}$ is the predominant molecular moiety produced by normal cells and has the best blend of the various VEGFs in that it is secreted and diffusable, while only modestly binding to extracellular matrix (ECM).

Other angiogenic factors for use with the current invention include but are not limited to Platelet-derived Endothelial Cell Growth Factor, Angiogenin, basic and acidic Fibroblast Growth Factor (also known as Heparin Binding Growth Factor I and II, respectively), Transforming Growth Factor-Beta, Platelet-derived Growth Factor, Hepatocyte Growth Factor, Fibroblast Growth Factor-18, Butyryl Glycerol, prostaglandins PGE1 and PGE2, nicotinamide, Adenosine, (12R)-hydroxyeicosatrienoic acid, and okadaic acid.

In step S6300, the transduced cells are seeded into an encapsulation/entrapment body such as the exemplary encapsulation/entrapment bodies 112 of FIGS. 1A, 2A, and 3A. Seeding can be accomplished by rinsing infected human myoblast cells grown on gelatin coated dishes with PBS, trypsinizing then, counting them on a hemocytometer, centrifuging, and then resuspending them in 5 ml serum-free myoblast growth medium containing 0.3% fibrinogen. This has, in the past, yielded concentrations of about $1 \times 10^7$ cells/ml. Such cell suspensions can then be concentrated by removing growth medium by pressure driving the suspension solution through an open portion 113 and/or 114 of encapsulation/entrapment bodies 112 provided the other open portion is capped.

In embodiments such as that illustrated in FIGS. 3A, 3B, and 3C where the cells capable of providing a sufficient supply of angiogenic factor are not encapsulated, a conduit 122 can simply be placed in a cell suspension.

After filtration and/or gelation, the resulting encapsulation/entrapment bodies 112 can be either refilled and/or rinsed with serum free-myoblast growth medium containing thrombin (0.3 unit/ml) and placed in a 37° C. incubator for 30 minutes for the formation of fibrin glue inside and/or outside the encapsulation/entrapment bodies 112.

As described above, other geometries of the bioartificial filtration device are available, and thus other cell immobilization and/or entrapment protocols may be necessary. For example, if portions 113 and/or 114 are closed, the suspension could be placed in, for example, an extruded polymeric capsule, a collagen gel monolith and/or microspheres which are cast in the desired geometry. An example of a commercially available collagen gel product is GELFOAM available from UpJohn.

In step S6400, the seeded cells are expanded as needed. This can be done by perfusing the encapsulation/entrapment bodies 112 with myoblast growth medium through tubing connected to an open portion 123. Media can be circulated with pump at a flow rate dependent upon the nature and geometry of the encapsulation/entrapment bodies 112, which, in one embodiment, are maintained in a 37° C., 5% $CO_2$, humidified incubator and the media is changed every three days. The cell viability can be monitored by measuring lactate production if desired.

In step S6500, the cells are differentiated. In one embodiment, the cells are myoblasts and morphological differentiation, the fusion of mononucleated myoblasts into multinucleated myotubes, can be followed under a microscope on living cells or after fixation and staining of the cells if necessary. In addition, the twitch of myotubes can be spontaneously observed in culture and augmented by acetylcholine. The cells are first plated on gelatin-coated dishes in proliferation medium at a density of approximately $10^5$ cells per 35 mm dish. The cells are allowed to grow for several days. Spontaneous differentiation frequently occurs after growth for approximately 5 to 8 days in proliferation medium; however, after 4 to 5 days of growth, differentiation can be stimulated by feeding the cells with differentiation medium for 48 to 72 hrs. A common differentiation medium is DMEM media supplemented with 2% horse serum and 10 ug/ml insulin. At this concentration, insulin mimics the positive effects of IGFs on differentiation. The conversion of myoblasts to myotubes can be recorded by staining of Leukostat stain kit (Cat.CS430D, Fisher Scientific). Twitch, a behavior unique to myoblast differentiation, can be spontaneously observed and become typical by adding acetylcholine in acetate buffer (pH 4.0) to a final concentration of 1 mM.

In step S6600, the device is implanted into the recipient. In one exemplary embodiment, a prototype as illustrated in either FIG. 4A. or FIG. 4B. containing more than 50 hollow fiber pairs is prepared and encased with an autologous fibrin clot and placed subcutaneously, peritoneally, or retroperitoneally in a recipient. In some embodiments, the conduits 122 will be tunneled subcutaneously and placed in fluid communication with peritoneal dialysis tubing and a collection bag. This is desirable since peritoneal dialysis tubing can be collected every 24 hours and exchanged to a new drainage bag using the UV flash technique designed for peritoneal dialysis to maintain sterility of the bag exchange and to minimize infection. In another exemplary embodiment, capillary ingrowth can be induced by the daily infusion through the drainage port of the VEGF-containing culture supernatant from the transduced myoblasts to be used in the implant. The culture fluid contains large amounts of VEGF and can help maximize vascularization of the implant prior to introduction of myoblasts into the device. This is desirable in cases where the implantation in an unprepared subcutaneous bed or the peritoneal cavity leads to myocyte necrosis due to hypoxic conditions.

Assessment of the functional performance of the implant can be performed using filtrate volume measurements every 24 hours, or as necessary. The filtrate can also be analyzed for electrolytes, BUN and creatinine, and albumin content by protein electrophoresis. The permselectivity characteristics to albumin is a critical parameter for assessing the type of drainage hollow fiber to be used in the device. For example, if large losses of albumin are observed, the conduits 122 can be replaced by conventional hemofiltration fibers made of polysulfone or polyacrylonitrile and with a M.W.C.O. of 40,000-60,000. Filtrate flow rates achieved in large animals should be approximately 2-4 ml/min.

A sufficient supply of angiogenic factor supplied by the cells 200 for inducing and/or maintaining vascularization near the implant according to the present invention depends upon several factors including but not limited to the nature and number of the angiogenic factor(s), the geometry of the bioartificial filtration device, the permeability and chemical structure of the conduits 122 and encapsulation/entrapment bodies 112 of permeable hollow fiber 100, the nature of the organic component(s) to promote cellular growth and/or adhesion on or in permeable hollow fiber 100, the location of an implanted bioartificial filtration device within the body (J. A. Thompson et al., Science 241, p. 1349-1352, 1988, the contents of which are incorporated herein by reference), whether angiogenic factors were previously administered to a region prior to implantation of the bioartificial filtration device, and the pressure gradient (if any) driving filtrate into conduits 122 of permeable hollow fiber 100.

In the exemplary embodiment using vascular endothelial growth factors (VEGF) a preferred concentration thereof in the surrounding tissue should be in a physiologically active range between 0.01 and 10 ng/ml, and more preferably between 0.1 and 5 ng/ml.

A preferred rate of supply of hVEGF is between 5 and 50,000 ng/day, but more preferably between 50 and 5,000 ng/day, and most preferably between 100 and 1000 ng/day, as described by Weir, G. C. et al., Cell Transplantation 9, p. 115-124, 2000, the contents of which are incorporated herein by reference.

In embodiments using basic Fibroblast Growth Factor as the angiogenic factor, a preferred concentration thereof in the surrounding tissue should be in a physiologically active range of between 0.01 and 10 ng/ml, and more preferably between 0.1 and 1 ng/ml. In a bioartificial filtration device formed from an Amicon DIAFILTER MINIFILTER with the blood input capped, the preferred rate of supply of basic Fibroblast Growth Factor is between 0.1 and 1000 ng/day, and more preferably between 1 and 500 ng/day, and most preferably between 10 and 100 ng/day when this bioartificial filtration device collects approximately 10-50 ml of filtrate/day.

Figure 8:
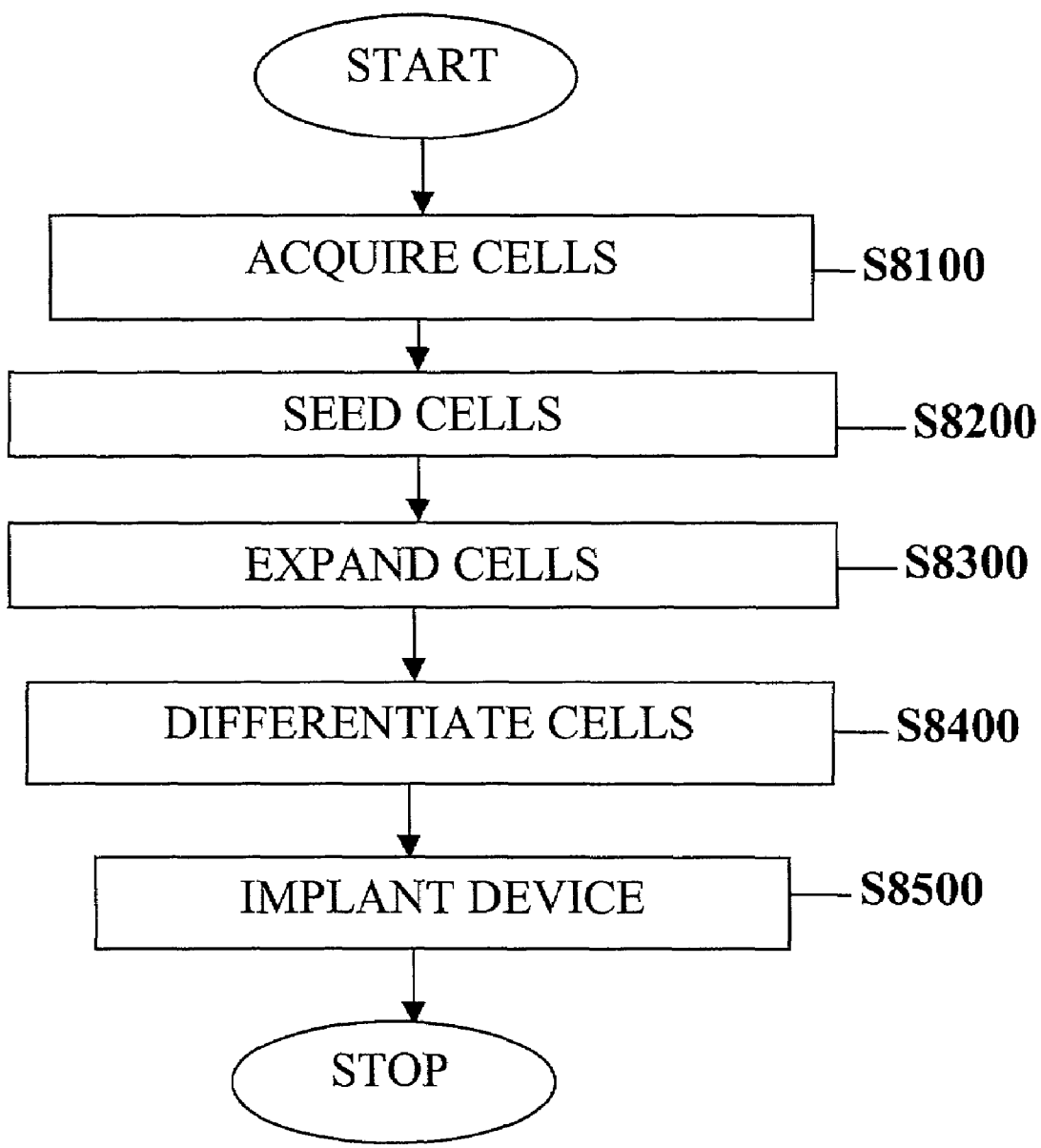
FIG. 8 illustrates an exemplary process flow according to a second embodiment of the invention for producing, for example, the embodiments illustrated in FIGS. 1B, 2B, and 3B.

FIG. 8 illustrates a an exemplary process flow according to a second embodiment of the invention. In step S8100, cells capable of providing a sufficient supply of angiogenic factors to induce and/or maintain vascularization are simply acquired. They could, for example, be transduced cells purchased from a vendor, or a cell line that produces at least one angiogenic factor in sufficient quantity to perform the present invention. In step S8200, the cells are seeded substantially as described in regard to step S6300 of FIG. 6, with changes in protocol as appropriate. In step S8300, the cells are expanded substantially as described in regard to step S6400 of FIG. 6, with changes in protocol as appropriate. In step S8400, the cells can be differentiated substantially as described in regard to step S6500 of FIG. 6, with changes in protocol as appropriate. In step S8500, the device is implanted substantially as described in regard to step S6600 of FIG. 6, with changes in protocol as appropriate.

Figure 9:
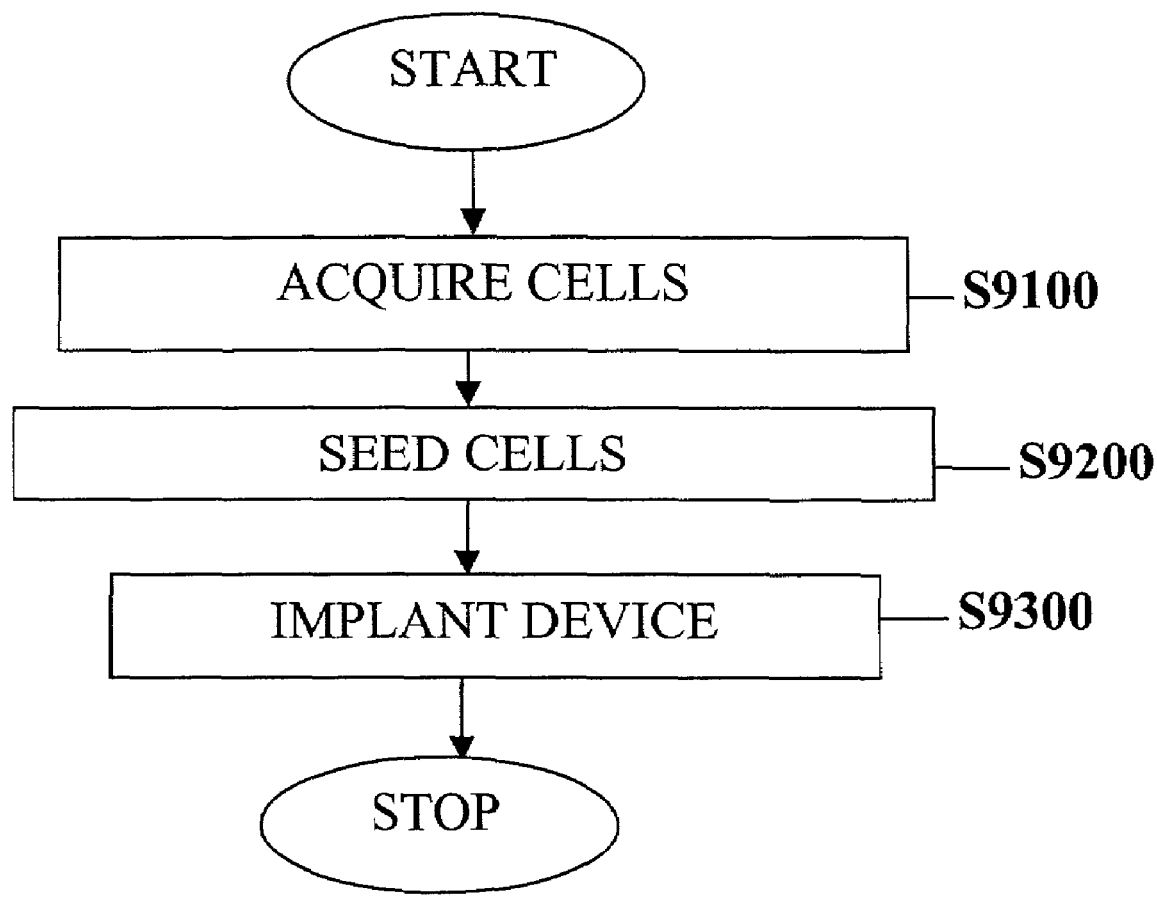
FIG. 9 illustrates an exemplary process flow according to a third embodiment of the invention for producing, for example, the embodiments illustrated in FIGS. 1B, 2B, and 3B.

FIG. 9 illustrates an exemplary process flow according to a third embodiment of the invention. In step S9100, cells capable of providing a sufficient supply of angiogenic factors to induce and/or maintain vascularization are simply acquired. They could, for example, be transduced cells purchased from a vendor, or a cell line that produces at least one angiogenic factor in sufficient quantity to perform the present invention, or even mature cells with the same properties. In step S9200, the cells are seeded substantially as described in regard to step S6300 of FIG. 6, with changes in protocol as appropriate, and in step S9300 the device is implanted substantially as described in regard to step S6600 of FIG. 6, with changes in protocol as appropriate. Thus, in some cases, expansion of the cell could occur in vivo and not require special acts by the user of the present invention. Likewise, differentiation could occur spontaneously, or even not be necessary, in the case of selected cell lines and/or implant sites.

Figure 10:
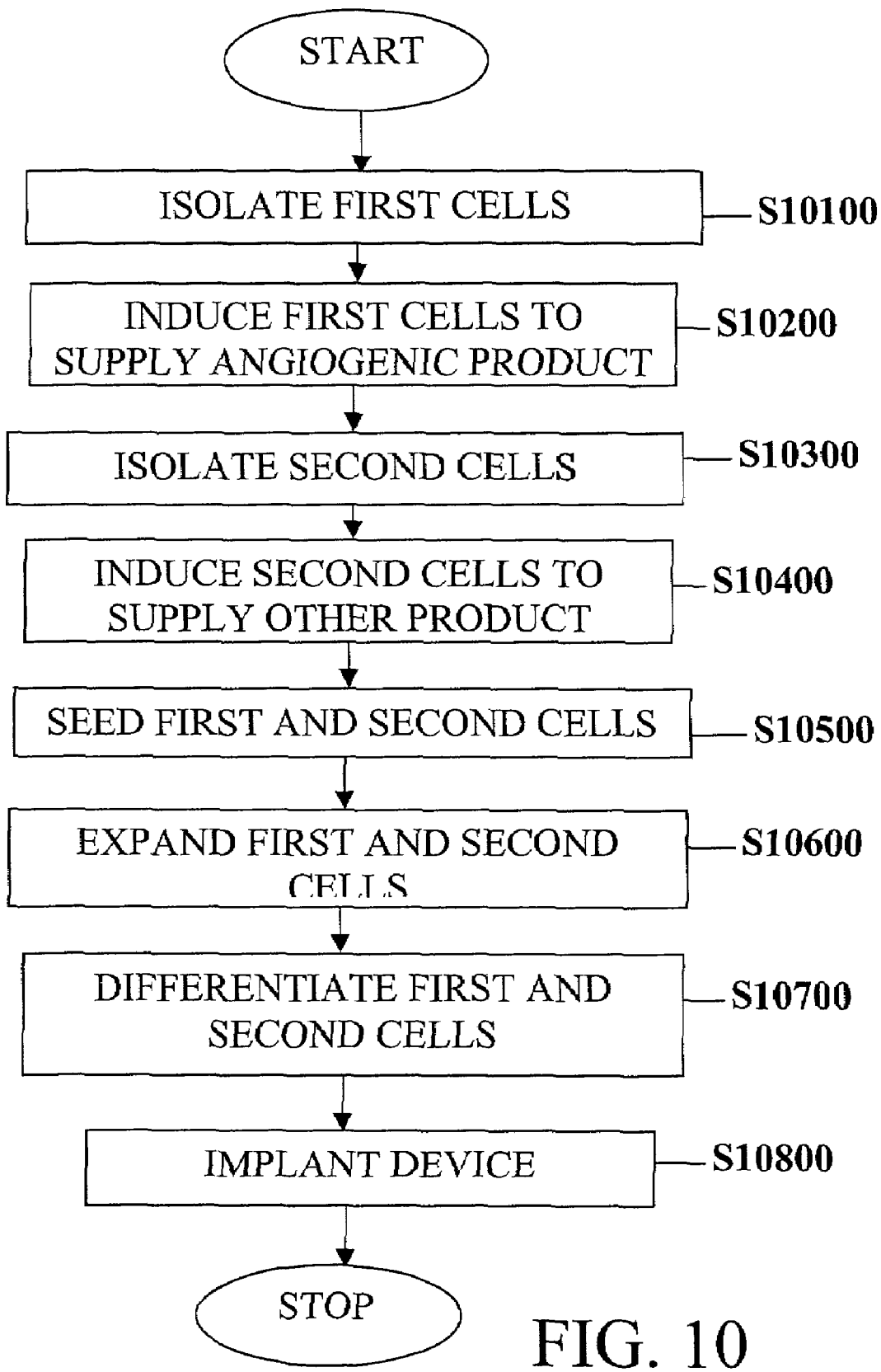
FIG. 10 illustrates an exemplary process flow according to one embodiment of the invention for producing, for example, the embodiments illustrated in FIGS. 1C, 2C, and 3C.

FIG. 10 illustrates an exemplary process flow according to one embodiment of the invention suitable for producing, for example, the embodiments illustrated in FIGS. 1C, 2C, and 3C wherein a second cell line capable of supplying a second cellular product is immobilized in and/or around an implant according to the present invention. In step S10100, the first cells, namely the cells capable of supplying or being made to supply, one or more angiogenic factors in sufficient quantities to induce and/or maintain vascularization near an implant, are isolated. This isolation can proceed substantially as described in regard to step S6100 of FIG. 6. The isolated cells are then transduced to induce production of at least one angiogenic factor, substantially as described in regard to step S6200. In step S10300, a second cell line is isolated, and the production of another cellular product by the second cells is induced in step S10400. Induction can proceed, for example, by transducing the second cells with DNA coding for the second cellular product. Examples of isolating a second cell line and inducing production of a cellular product according to the present invention are known in the art and illustrative examples are described in U.S. Pat. Nos. 5,639,275, 5,656,481, 5,550,050, 5,653,975, 5,676,943, 5,773,286, 5,795,790, the contents of all of which are incorporated herein by reference. In step S10500, both the first cells and the second cells are seeded in the implant substantially as described in regard to step S6300 of FIG. 6 with changes to the protocol as necessitated, for example, by the behavior of the second cells, and in step S10600 they are expanded as needed substantially as described in regard to step S6400 of FIG. 6 with changes to the protocol as necessitated, for example, by the behavior of the second cells. In step S10700, the cells are differentiated substantially as described in regard to step S6500 of FIG. 6. with changes to the protocol as necessitated, for example, by the behavior of the second cells, and the device is implanted in step S10800, substantially as described in regard to step S6600 of FIG. 6.

Figure 11:
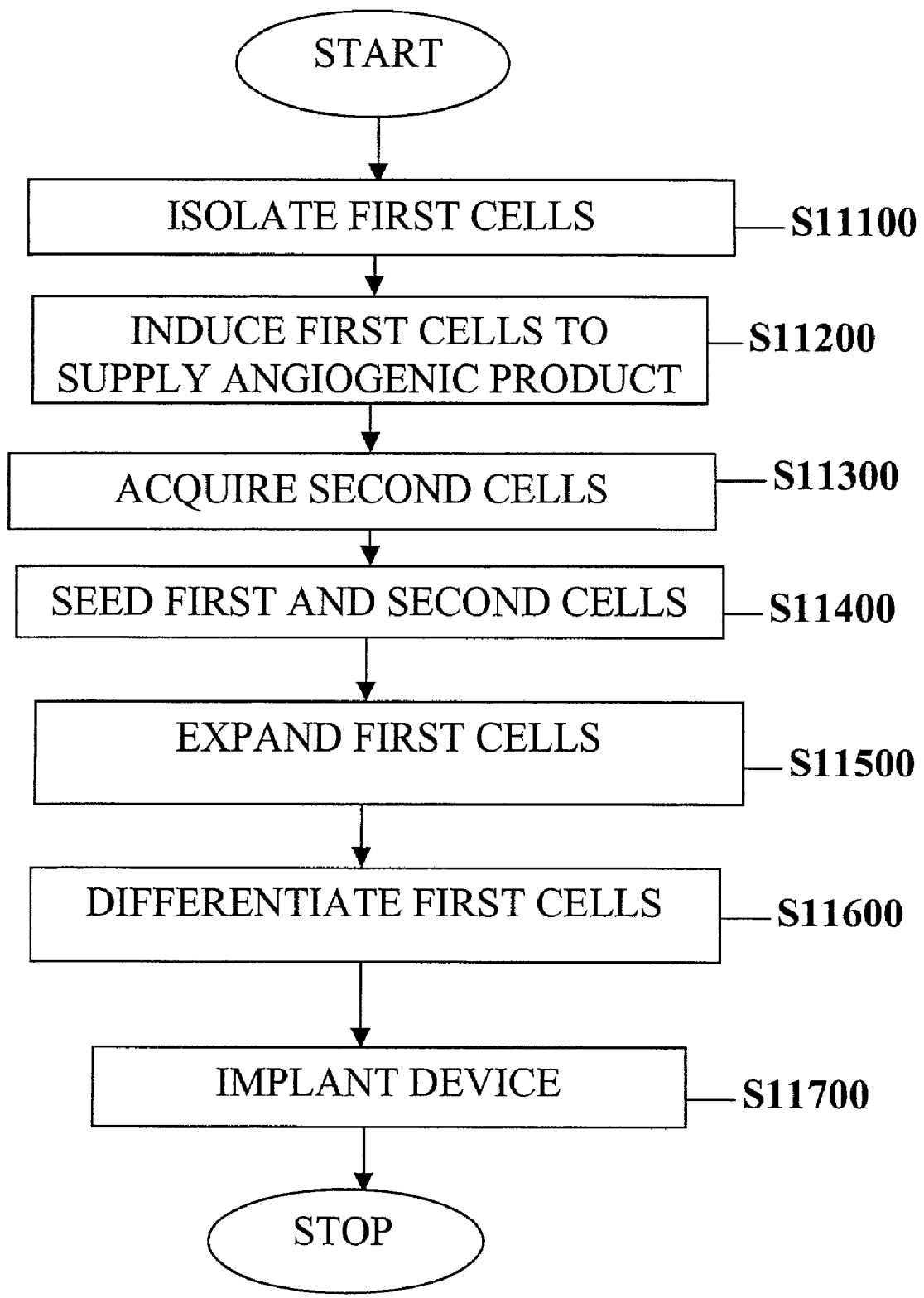
FIG. 11 illustrates an exemplary process flow according to a second embodiment of the invention for producing, for example, the embodiments illustrated in FIGS. 1C, 2C, and 3C.

FIG. 11 illustrates an exemplary process flow according to a second embodiment of the invention for producing, for example, the embodiments illustrated in FIGS. 1C, 2C, and 3C wherein a second cell type capable of providing a therapeutically useful function, such as supplying a second cellular product is immobilized in and/or around an implant according to the present invention. In this case, the second cells are simply acquired in step S11300 from, for example, a third party vendor and/or isolated from a donor. Inducement to produce the second cellular product as described in regard to step S10200 of FIG. 10 can thus be performed by this vendor, or may not even be necessary. Once the second cells are seeded in step S11400, expansion and/or differentiation of the second cells may or may not be necessary, and/or may proceed spontaneously in vivo and thus not require any special acts on the part of one who practices the current invention. The transduction of the first cells in step S11200, the expansion of the first cells in S11500, the differentiation of the first cells in step S11600, and implantation of the device in step S11700 can proceed substantially as described in regard to steps S6200, S6300, S6500, and S6600 of FIG. 6, with changes in protocol being made as necessary to account for the presence of the second cells.

The process flow of FIG. 11 can also be modified to account for cases where the first cells are prepared prior to implantation as described in FIGS. 8 and 9.

EXAMPLES

Having generally described this invention, a further understanding can be obtained by reference to certain specific examples which are provided herein for purposes of illustration only and are not intended to be limiting unless otherwise specified.

Example 1

Stereolithography, a uniquely powerful solid freeform fabrication technique, will be used for the iterative exploration and development of an implantable hemofilter device (1)-(5). The use of the Stereolithography Apparatus (SLA) will make it possible to design and fabricate many different hemofilter configurations quickly and precisely without requiring costly tooling.

Figure 12:
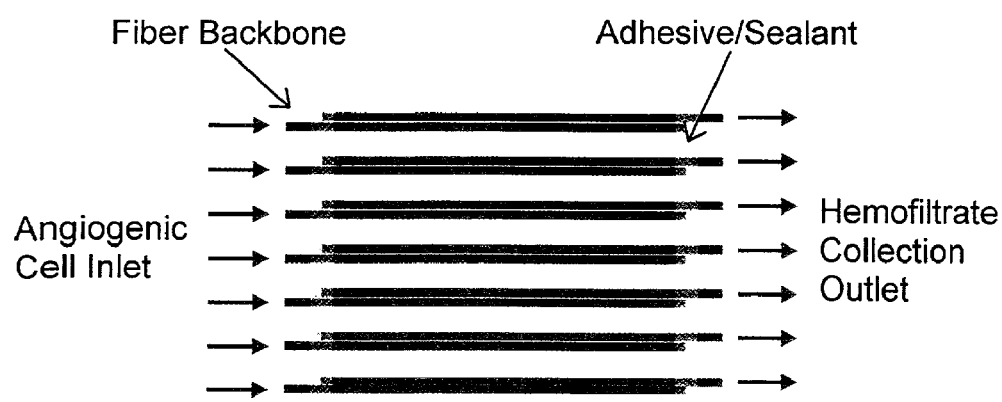
FIG. 12 illustrates a hemofilter design approach: alternating microporous hollow fibers configured on a fiber backbone.

The general approach will be to construct a series of flexible backbones in the SLA to support well defined arrangements of microporous hollow fibers. These hollow fibers will serve to either encapsulate genetically modified cells containing an angiogenic growth factor or to serve as hemofiltrate collection ducts. A design of such a device is illustrated FIG. 12. Pairs of fibers are arranged parallel to one another and fixed in place on the thin fiber backbone. Each alternating fiber is capped by the adhesive to create an interdigitated array of hemofiltrate and angiogenic fibers as illustrated in FIG. 12.

Figure 13:
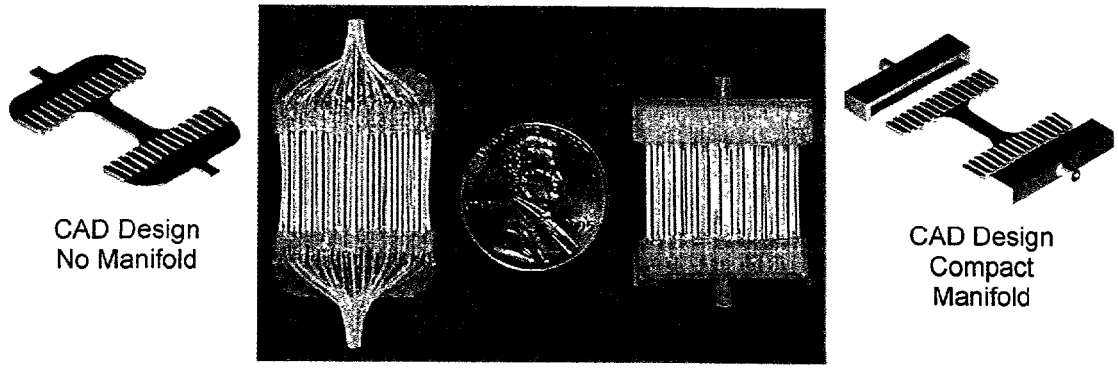
FIG. 13 illustrates two different bioartificial kidney prototypes assembled from stereolithography backbones and microporous hollow fibers.

Two device designs were assembled, and are shown in FIG. 13. A commercial Computer Aided Drawing package (CAD) was used to construct electronic drawings of two prototype fiber backbone designs, and are shown in FIG. 13. Both CAD designs employ spacer blocks along the ends of the backbone to ensure precise fiber placement. The design on the left of the Figure relies on the careful routing of the angiogenic and hemofilter fiber ends to a single collection point. The design on the right of the Figure utilizes a compact manifold assembly for both fiber types. These prototypes were constructed from a UV cured epoxy resin. Several potential material alternatives exist for the creation of future devices; including the direct SLA of commercially available medical grade silicone or the use of medical grade curable polyurethane resins. The infinite versatility and reproducibility of the SLA machine will make it possible to isolate and study the various tissue engineering issues critical to the successful execution of a bioartificial kidney implant.

REFERENCES (1) P. F. Jacobs, Stereolithography and other RP&M Technologies, From Rapid Prototyping to Rapid Tooling, ASME Press, New York, N.Y., 1996.
(2) S. E. Feinberg, S. J. Hollister, J. W. Halloran, G. Chu, P. H. Krebsbach, "Role of Biomimetrics in Reconstruction of the Temporomandibular Joint," *Oral and Maxillofacial Surgery Clinics of North America*, Vol. 12, No. 1, pg. 149-160 February 2000.
(3) G. T -M. Chu, G. A. Brady, W. Miao, J. W. Halloran, S. J. Hollister, D. Brei, "Ceramic SFF by Direct and Indirect Stereolithography," *Solid Freeform and Additive Fabrication*, Ed. D. Dimos, S. C. Danforth, and M. J. Cima, MRS Symposia Proceedings, Vol. 542, pg. 119-123, 1999.
(4) G. A. Brady and J. W. Halloran, "Solid Freeform Fabrication of Ceramics via Stereolithography," *Naval Research Reviews*, Office of Naval Research, pg. 39-43, Three/1998, Vol L, 1998.
(5) M. L. Griffith, C. T -M, Chu, W. Wagner, J. W. Halloran, "Ceramic Stereolithography for Investment Casting and Biomedical Applications," *Solid Freeform Fabrication Proceedings*, Ed. J. J. Beaman, J. W. Barlow, Austin, Tex., SFF Symposium, pg. 31-36, 1996.

Obviously, numerous modifications and variations of the present invention are possible in light of the above teachings. It is therefore understood that within the scope of the appended claims, the invention may be practiced otherwise than as specifically described herein.

What is claimed as new and desired to be secured by Letters Patent of the United States is:

1. An implantable hemofilter device capable of collecting an ultrafiltrate and comprising an ultrafiltrate collection network, and first cells,
   wherein the first cells produce at least one angiogenic product,
   wherein the ultrafiltrate collection network comprises a first permeable membrane component at least partially defining a first cavity and a second permeable membrane component at least partially defining a second cavity, and wherein the first and second cavities are exclusive of each other and are in fluid communication with each other,
   wherein the first cavity contains the first cells,
   wherein the second cavity collects the ultrafiltrate and remains essentially clear of the first cells, and wherein the angiogenic product of the first cells in the first cavity induces or maintains surrounding vascularization.

2. The device of claim 1, wherein the first cavity and the second cavity have a rectangular shape as defined by the first and second permeable membranes, respectively.

3. The device of claim 1, wherein the first cavity is in the form of a cylinder as defined by the first permeable membrane.

4. The device of claim 1, wherein the first cavity and the second cavity each have a helical geometry as defined by the first and second permeable membranes, respectively.

5. The device of claim 1, wherein at least one end of at least one of each of the first cavity and the second cavity are open.

6. The device of claim 1, wherein at least one end of at least one of each of the first cavity and the second cavity is capped.

7. The device of claim 1, wherein the first cavity has a spherical shape.

8. The device of claim 1, wherein the second cavity remains substantially clear of cells and cellular products other than said first cells and cellular products from said first cells.

9. The device of claim 1, wherein the first and the second cavities are contiguous and are partitioned from each other by a wall, to thereby form a double hollow fiber.

10. The device of claim 9, wherein the ultrafiltrate collection network comprises a plurality of double hollow fibers, and wherein the double hollow fibers are arranged substantially in parallel.

11. The device of claim 9, wherein the ultrafiltrate collection network comprises a plurality of the double hollow fibers and the double hollow fibers are connected to a manifold.

12. The device of claim 9, wherein the ultrafiltrate collection network comprises a plurality of the double hollow fibers, and the double hollow fibers are in fluid communication with each other.

13. The device of claim 9, wherein the ultrafiltration coefficient of the double hollow fiber is at least 20 mL/hr, Torr,$m^2$.

14. The device of claim 9, wherein the ultrafiltration coefficient of the double hollow fiber is at least 20 to 100 mL/hr,Torr,$m^2$.

15. The device of claim 9, wherein the double hollow fiber has a molecular weight cutoff of substantially equal to or less than 60,000 g/mole.

16. The device of claim 9, wherein the double hollow fiber is composed of a polymer.

17. The device of claim 9, wherein the double hollow fiber is composed of a material selected from the group consisting of polypropylenes, polysulfones, cellulosic polymers, rayons, polyacrylonitriles, polymethylmethacrylates, polycarbonates, polyfluoroethylenes and copolymers thereof.

18. The device of claim 1, which is in fluid communication with an implant body, wherein the implant body is composed of at least one material selected from the group consisting of glasses, metals, ceramics, and polymers.

19. The device of claim 18, wherein the implant body is composed of at least one polymer selected from the group consisting of a polypropylenes, polysulfones, cellulosic polymers, cellulose actetates, rayons, polyacrylonitriles, polymethylmethacrylates, polycarbonates, polyfluorethylenes, alginates, and chitosans.

20. The device of claim 1, wherein the angiogenic product is vascular endothelial growth factor.

21. The device of claim 1, wherein the first cells are transfected with a nucleic acid sequence which encodes the angiogenic product.

22. The device of claim 1, wherein the first cells are myoblasts.

23. The device of claim 22, wherein the myoblasts form a myotube.

24. The device of claim 18, wherein the first cells are supported on the implant body with an organic component.

25. The device of claim 24, wherein the organic component comprises fibrin glue.

26. The device of claim 1, wherein the hemofilter device contains in the second cavity additional cells which have a function other than producing an angiogenic product.

27. The device of claim 26, wherein the additional cells have a therapeutic function.

28. The device of claim 26, wherein the additional cells produce a therapeutically useful substance.

29. The device of claim 28, wherein the therapeutically useful substance is a hormone.

30. The device of claim 26, wherein the additional cells produce insulin.

31. The device of claim 26, wherein the additional cells are genetically modified.

32. The device of claim 26, wherein the additional cells have metabolic activity.

33. The device of claim 9, wherein the wall includes a permeable membrane material, whereby the first and second cavities are in fluid communication with each other through the wall.

34. The device of claim 9, wherein the wall includes an impermeable material, whereby the first and second cavities are in only indirect fluid communication with each other.

35. The device of claim 1, wherein the second cavity contains second cells, wherein the second cells are selected from the group consisting of stem cells, hematopoietic stem cells, hepatocytes, pancreatic islet cells and proximal tubule cells.

* * * * *

UNITED STATES PATENT AND TRADEMARK OFFICE
CERTIFICATE OF CORRECTION

PATENT NO. : 7,332,330 B2　　　　　　　　　　　　　　　　　　　　　　　　Page 1 of 1
APPLICATION NO. : 09/949575
DATED : February 19, 2008
INVENTOR(S) : H. David Humes et al.

It is certified that error appears in the above-identified patent and that said Letters Patent is hereby corrected as shown below:

On the Title Page; field (73), insert the following after
RenaMed Biologics, Inc., Lincoln, RI (US):

--Assignees: The Regents of the University of Michigan, Ann Arbor, MI (US)--

Signed and Sealed this

Sixth Day of January, 2009

JON W. DUDAS
*Director of the United States Patent and Trademark Office*